US012226117B2

(12) United States Patent
Escudero et al.

(10) Patent No.: US 12,226,117 B2
(45) Date of Patent: Feb. 18, 2025

(54) ATHERECTOMY APPARATUS WITH IMAGING

(71) Applicant: AtheroMed, Inc., Menlo Park, CA (US)

(72) Inventors: Paul Quentin Escudero, Menlo Park, CA (US); August Christopher Pombo, Menlo Park, CA (US); Torrey P. Smith, Menlo Park, CA (US); Douglas E. Rowe, Menlo Park, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 383 days.

(21) Appl. No.: 15/048,042

(22) Filed: Feb. 19, 2016

(65) Prior Publication Data
US 2016/0242808 A1    Aug. 25, 2016

Related U.S. Application Data

(60) Provisional application No. 62/118,585, filed on Feb. 20, 2015.

(51) Int. Cl.
| *A61B 17/3207* | (2006.01) |
| *A61B 8/00* | (2006.01) |
| *A61B 8/12* | (2006.01) |
| *A61B 17/00* | (2006.01) |
| *A61B 17/22* | (2006.01) |
| *A61B 90/00* | (2016.01) |

(52) U.S. Cl.
CPC ........ *A61B 17/320758* (2013.01); *A61B 8/12* (2013.01); *A61B 8/4488* (2013.01); *A61B 2017/00685* (2013.01); *A61B 2017/22038* (2013.01); *A61B 2017/22042* (2013.01); *A61B 2090/064* (2016.02); *A61B 2090/3735* (2016.02); *A61B 2090/3784* (2016.02)

(58) Field of Classification Search
CPC .............................................. A61B 2090/3784
See application file for complete search history.

(56) References Cited

U.S. PATENT DOCUMENTS

| 5,000,185 A | 3/1991 | Yock |
| 5,226,909 A * | 7/1993 | Evans ............ A61B 17/320783 |
| | | 606/159 |
| 8,795,306 B2 | 8/2014 | Smith |
| 2008/0132790 A1 * | 6/2008 | Burton ................. A61B 8/0833 |
| | | 600/447 |
| 2009/0018566 A1 | 1/2009 | Escudero |

(Continued)

FOREIGN PATENT DOCUMENTS

| WO | 01/15609 | 3/2001 |
| WO | 2009/005779 | 1/2009 |
| WO | 2015/017114 | 2/2015 |

*Primary Examiner* — Martin T Ton

(57) ABSTRACT

The present invention relates to apparatuses for cutting and removing occlusive material with imaging capabilities. According to certain aspects, the apparatus includes a catheter body, a rotatable shaft, and an imaging element. The catheter body defines a lumen and includes a distal housing that defines an opening. The rotatable shaft is disposed within the lumen of the catheter body. The rotatable shaft includes a conveying component and a cutting element that is at least partially surrounded by the distal housing. The imaging element is located on the distal housing of the catheter body.

18 Claims, 25 Drawing Sheets

(56) References Cited

U.S. PATENT DOCUMENTS

| | | | |
|---|---|---|---|
| 2009/0018567 A1* | 1/2009 | Escudero | A61B 17/320758 606/159 |
| 2009/0216180 A1 | 8/2009 | Lee | |
| 2011/0130777 A1 | 6/2011 | Zhang | |
| 2012/0046679 A1* | 2/2012 | Patel | A61B 17/320758 606/159 |
| 2013/0096587 A1* | 4/2013 | Smith | A61B 17/320758 606/159 |
| 2013/0245430 A1 | 9/2013 | Selmon | |
| 2014/0276015 A1* | 9/2014 | Whiseant | A61B 17/3207 600/407 |
| 2014/0276059 A1* | 9/2014 | Sheehan | A61B 8/12 600/443 |

* cited by examiner

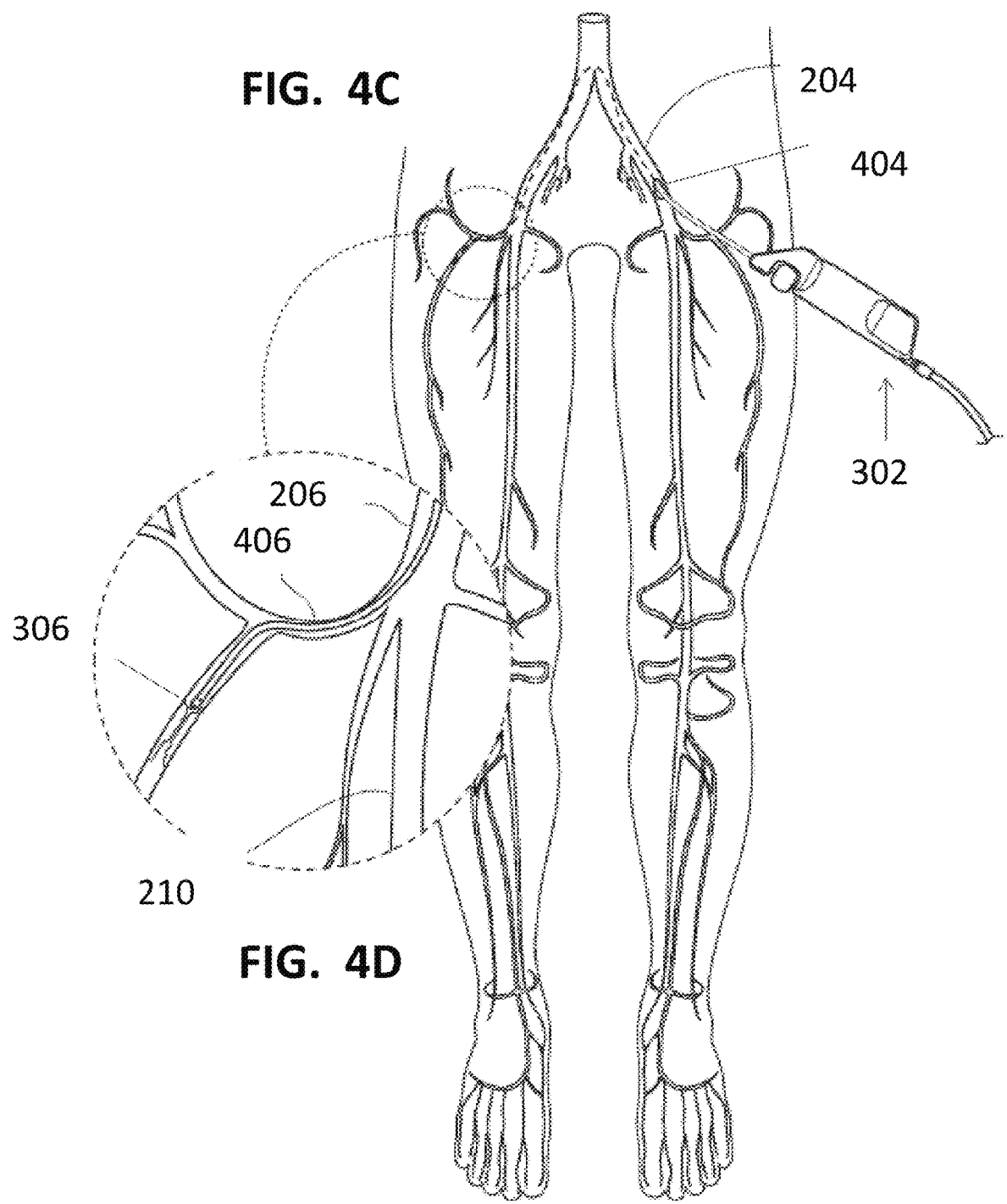

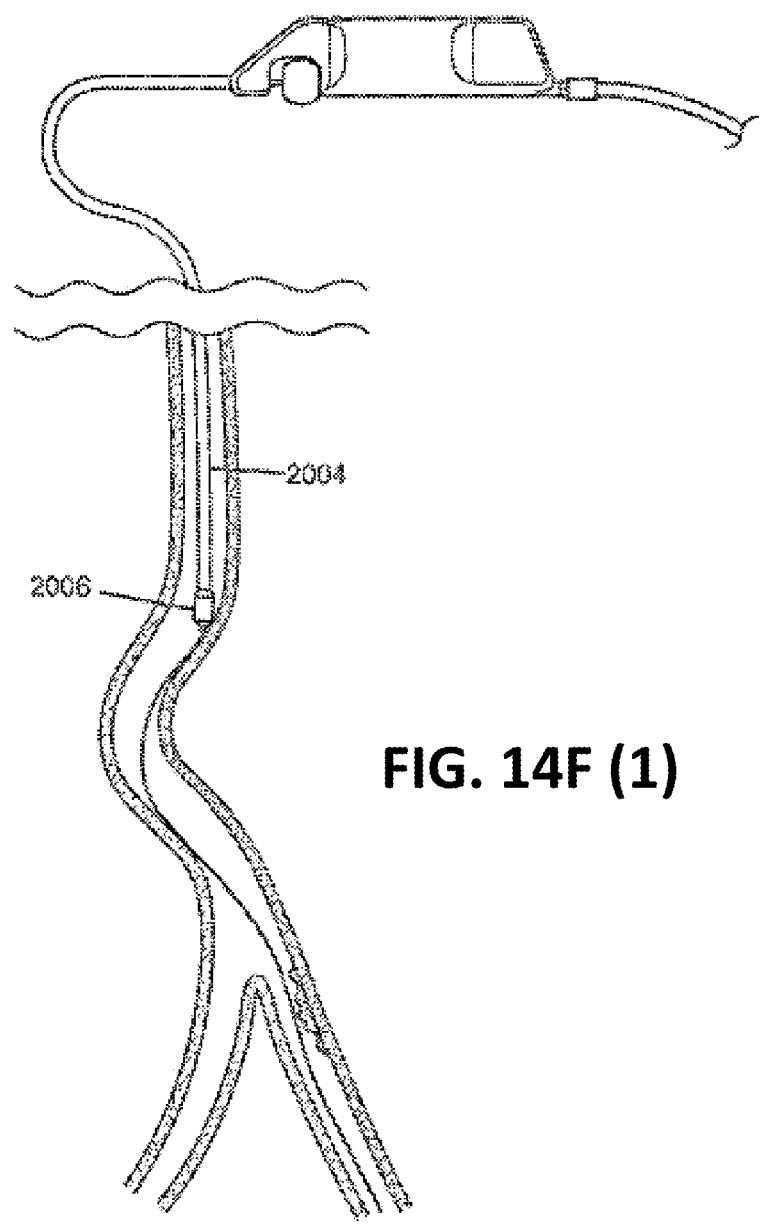
FIG. 14F (1)

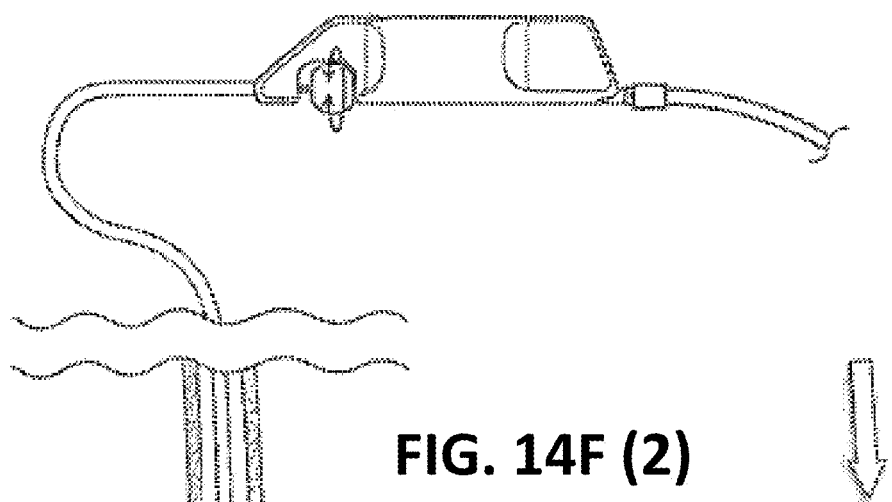
FIG. 14F (2)
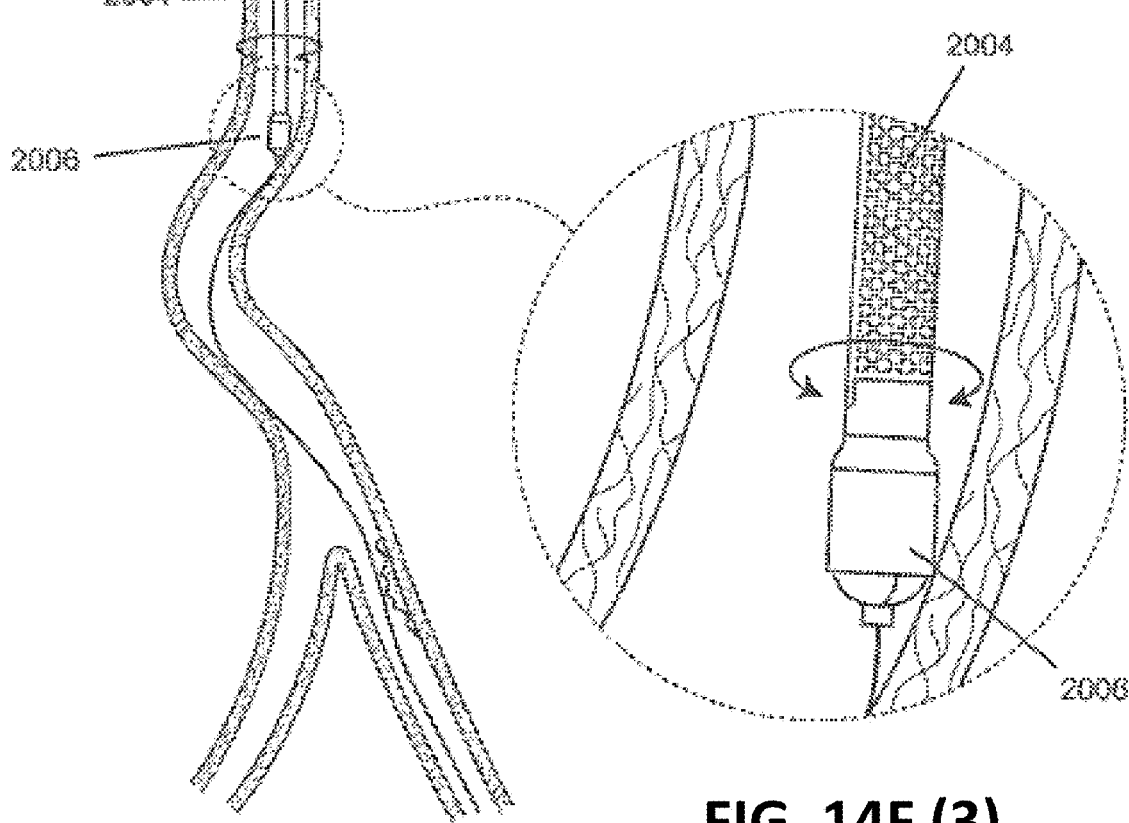
FIG. 14F (3)

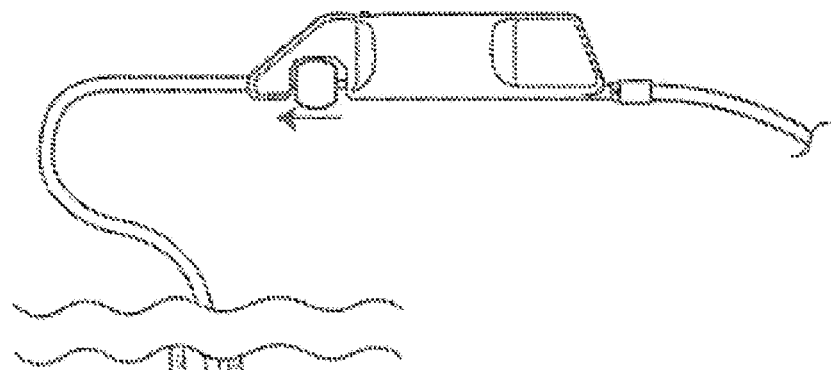
FIG. 14F (4)
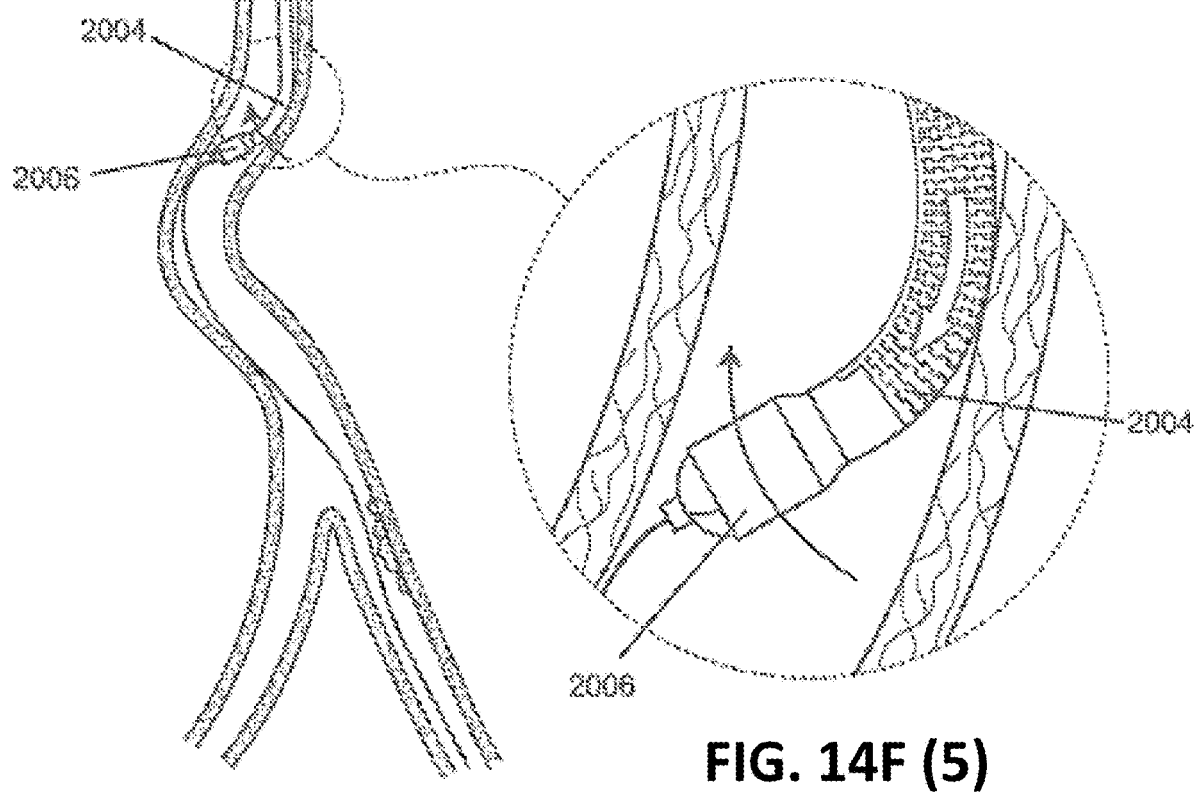
FIG. 14F (5)

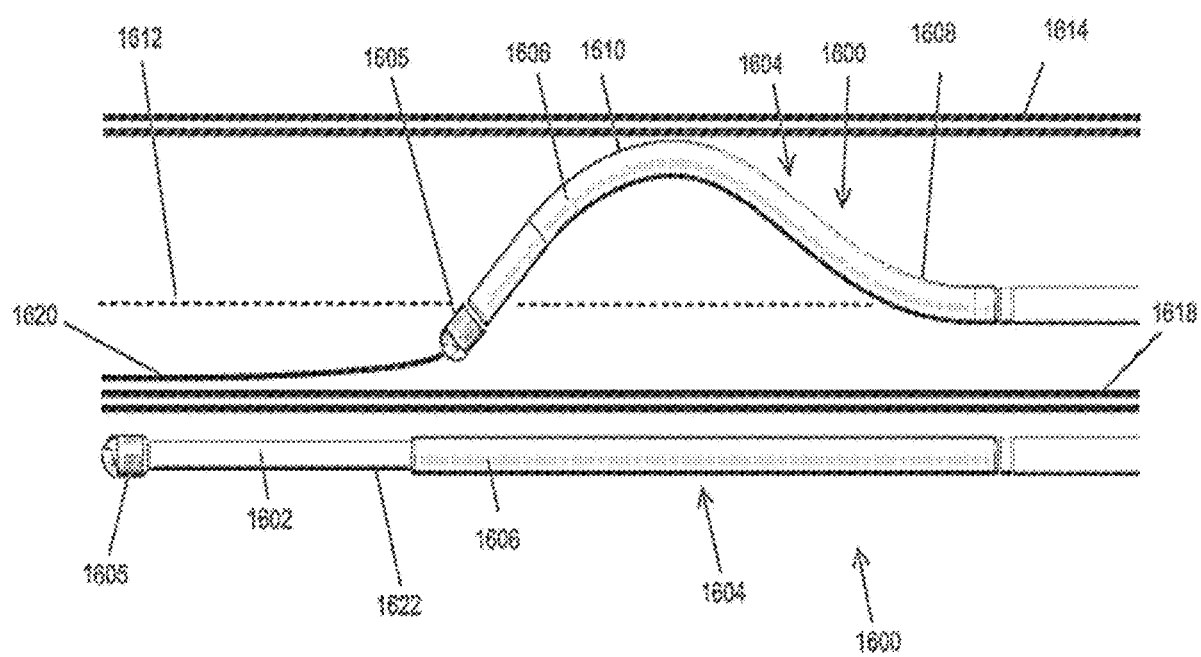

ATHERECTOMY APPARATUS WITH IMAGING

CROSS-REFERENCE TO RELATED APPLICATION

This application claims the benefit of and priority to U.S. Provisional Patent Application Ser. No. 62/118,585, filed Feb. 20, 2015, the contents of which are incorporated herein by reference in their entirety.

TECHNICAL FIELD

This application relates to the treatment of occluded body lumens, including the removal of occlusive material from a blood vessel.

BACKGROUND

Thrombosis is a medical condition that results from the formation of a blood clot, or thrombus, within a vessel. Deep vein thrombi often develop in the veins of legs or lower abdomen, but thrombi may occur in other vessels. The clot is typically formed from a pooling of blood within a vein due to abnormally long periods of rest, e.g. when an individual is bed ridden following surgery or suffering a debilitating illness. In addition to thrombosis, atherosclerosis is another medical condition that results from the formation of a blockage in a vein. Atherosclerosis is due to the build of atheroma material along the arterial walls. Atheroma deposits can have widely varying properties, with some deposits being relatively soft and others being fibrous and/or calcified. In the latter case, the deposits are frequently referred to as plaque. Often thrombosis and atherosclerosis are both present in the veins. For example, a thrombus develops around the atherosclerotic plaque.

The formation of thrombi and build-up of plaque can lead to stroke or embolism, which may cause serious health issues, including death. Strokes occur when the blood clot or plaque blocks an artery supplying blood to the brain, thus depriving brain tissue of oxygen. Without oxygen, brain cells begin to die. Embolisms occur when a blood clot travels around the body and lodges itself in an organ. For example, a pulmonary embolism is a blockage of the blood supply to the lungs that causes severe hypoxia and cardiac failure.

For some blockages, surgical intervention may be necessary to remove the thrombus, plaque, or both from a vessel, such as when cholesterol or anti-coagulant medications are not able to reduce the blockage. Balloon angioplasty is a common surgical treatment, and involves placing a balloon within the occlusion and inflating the balloon to macerate and/or displace plaque and other clots against the vessel wall. While generally effective, balloon angioplasty can undesirably stretch the artery, rip the vessel wall, and induce scar tissue formation, which may lead to restenosis of the artery. Atherectomy is another form of treating occluded vessels, and involves the use of an intravascular device to mechanically remove (e.g., de-bulk) blockages (e.g. plaque, thrombi, etc.) from the wall of the artery. While atherectomy devices are able to remove clots without stretching or ripping, there are some drawbacks. Atherectomy devices are often unable to remove the resulting morcellated plaque particles, and the generation of such particles significantly reduces angiogram visualization during the procedure.

SUMMARY

The present invention provides devices and methods for the mechanical breakdown and removal of blockages (e.g., plaque, thrombi, etc.), which simultaneously allow intraluminal imaging of the treatment site and procedure. Particular advantages of the invention include pre-treatment visualization of the type and severity of the occlusion, real-time intraluminal assessment of the mechanical breakdown of the occlusion for more complete and safe dissolution, and elimination of the exchange of multiple devices (e.g. need for a separate imaging catheter). Devices of the invention are well-suited to remove plaque and other atheroma deposits, but may also be used to treat thrombosis.

Devices of the invention generally include a catheter body and a rotatable shaft disposed within the catheter body. The rotatable shaft includes a cutting member coupled thereto and a conveying element along the length of the rotatable shaft. The distal end of the catheter body includes a housing that defines a distal opening and at least partially surrounds the cutting member. An imaging element is located on the housing and allows one to locate and assess the occlusion within a vessel, observe cutting and removal of the occlusion, and assess the vessel after treatment. For treatment, the cutting member rotates to mechanically breakdown the blockage, and the resultant blockage particles are driven from the vessel and into the catheter body via the conveying component.

The imaging assembly of the apparatus advantageously provides intraluminal guidance during treatment. The imaging assembly may be a forward-viewing imaging element, a side-viewing imaging element, or a combination thereof. Suitable imaging assemblies include ultrasound imaging assemblies and optical coherence tomography imaging assemblies.

In addition to imaging both vessels, the obtained image data can be subject to data processing (e.g., spectral analysis) such that blockage can be characterized. Processing techniques for characterizing objects present in the image data may include, for example, determining the density of the occlusion, determining the composition of the occlusion, determining a blood-tissue border of the lumen of the one or more vessels.

Generally, apparatuses of the invention include one cutting element, although some embodiments include more than one cutting element. The cutting element may include one or more flutes that form a cutting blade. The flutes typically have a positive rake angle. The positive rake angle may be at least 20 degrees. In some variations, the positive rake angle may range from 40 to 80 degrees. The cutting element may also include one or more crushing elements. The crushing elements may have a negative rake angle and are substantially rectangular in shape. The negative rake angle may range from at least 1, 5, 10, 15, 20, 25, 30 degrees or more. Where the cutting element is designed to slice/cut through the blockage, the crushing element is configured to provide blunt force to the blockage. It is contemplated that other positive and negative rake angles may be use for the cutting element and the crushing element.

Apparatuses of the invention include a conveying element associated with the rotatable shaft. The conveying element acts to remove the broken down particles from the vessel, thereby minimizing the amount of particles that are undesirably released into the blood stream. According to certain embodiments, the conveying element is a helical wire wound about the rotatable shaft, similar to a screw. When rotated, the conveying element drives particles proximally down the inner lumen of the catheter body. The particles may be deposited in a storage associated with the catheter body. The cross-section of the conveying element may be circular or rectangular. A rectangular cross-section increases the contact between the conveying element and an inner luminal surface of the catheter body, thereby increasing the conveying elements ability to drive particles within proximally within the catheter body.

BRIEF DESCRIPTION OF THE DRAWINGS

FIGS. 4A-4D depict illustrative methods by which an atherectomy system may be deployed intravascularly.

FIGS. 14A-14E and FIGS. 14F(1)-14F(5) depict a manner by which the atherectomy apparatus (2000) described above in relation to FIGS. 12A and 12B may be actively and passively steered within a vessel.

FIGS. 15A and 15B depict a variation of the atherectomy apparatuses described here.

DETAILED DESCRIPTION

The present invention provides atherectomy devices for removing occlusions within blood vessel while allowing real-time imaging of the procedure.

In certain embodiments, the devices and methods of the present invention are designed to break down and remove blood clots, such as such as emboli and thrombi, atheroma, plaque and other occlusive material from body lumens. The body lumens generally are diseased body lumens and in particular coronary arteries. The defect in the body lumen can be a de novo clot or an in-stent clot for example. The devices and methods, however, are also suitable for treating stenosis of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. The devices and methods of the present invention can collect lumenectomy samples or materials. While the remaining discussion is directed at aspirating, imaging, and passing through atheromatous or thrombotic occlusive material in a coronary artery, it will be appreciated that the systems, devices, and methods of the present invention can be used to aspirate and/or pass through a variety of occlusive, stenotic, or hyperplastic material in a variety of body lumens.

Figure 1:
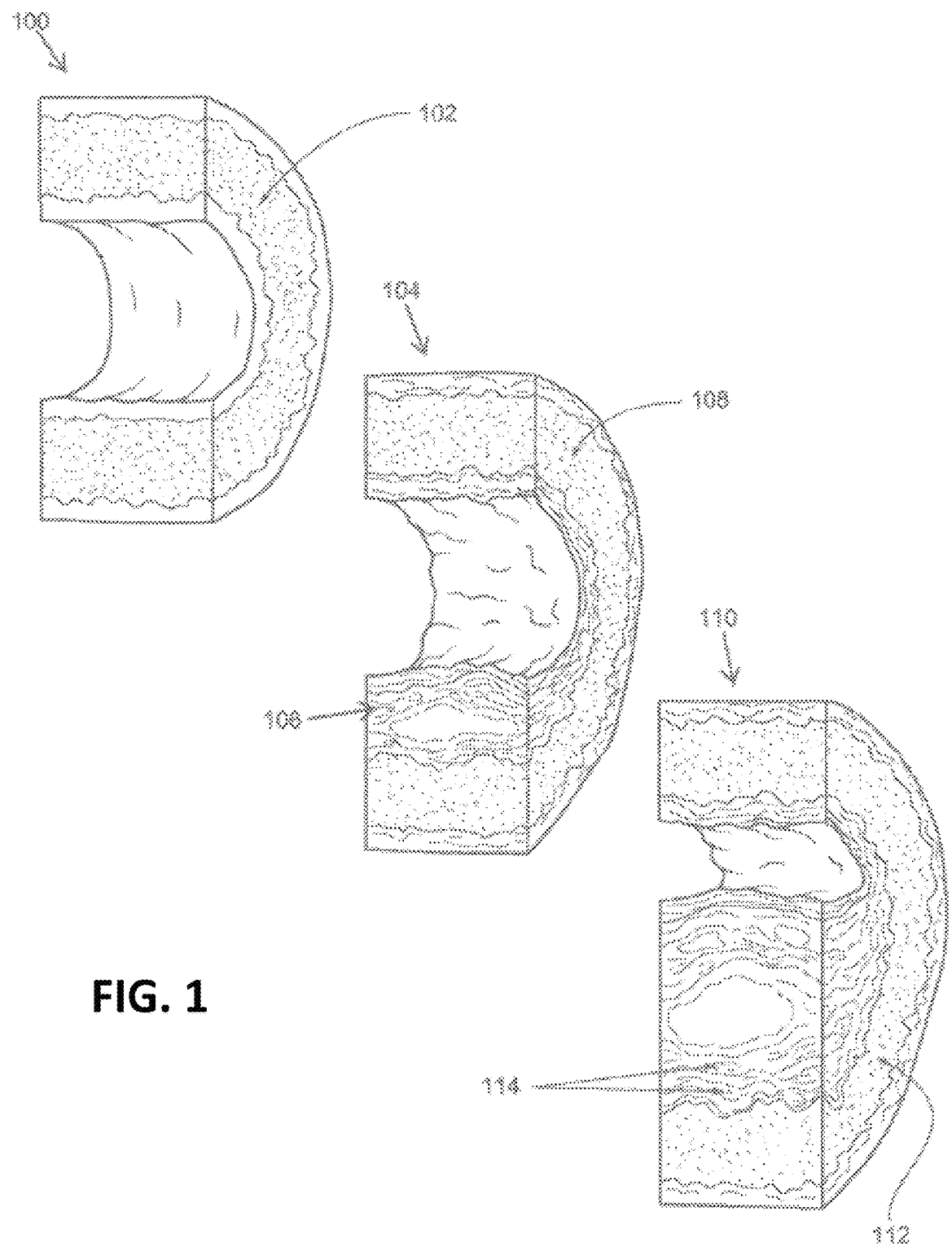
FIG. 1 shows anatomic views of segments of an artery, cut in section, to illustrate different degrees of atherosclerosis.

Atherectomy devices of the invention are particularly well-suited for the treatment of atherosclerosis. Atherosclerosis commonly affects the medium and large arteries, and may occur when fat, cholesterol, and other substances build up on the walls of arteries and form fleshy or hard/calcified structures called plaques/lesions. FIG. 1 shows an instance of a first normal arterial segment (100) having a native arterial wall (102), a second arterial segment (104) with mild atherosclerosis and initial plaque (106) formation on the native arterial wall (108), and a third arterial segment (110) with severe atherosclerosis and having advanced plaque (112) formation on the native arterial wall (114). As plaque forms within the native arterial wall, the artery may narrow and become less flexible, which may make it more difficult for blood to flow therethrough. In the peripheral arteries, the plaque is typically not localized, but can extend in length along the axis of the artery for as much as 10 mm or more (in some instance up to 400 mm or more).

Figure 2:
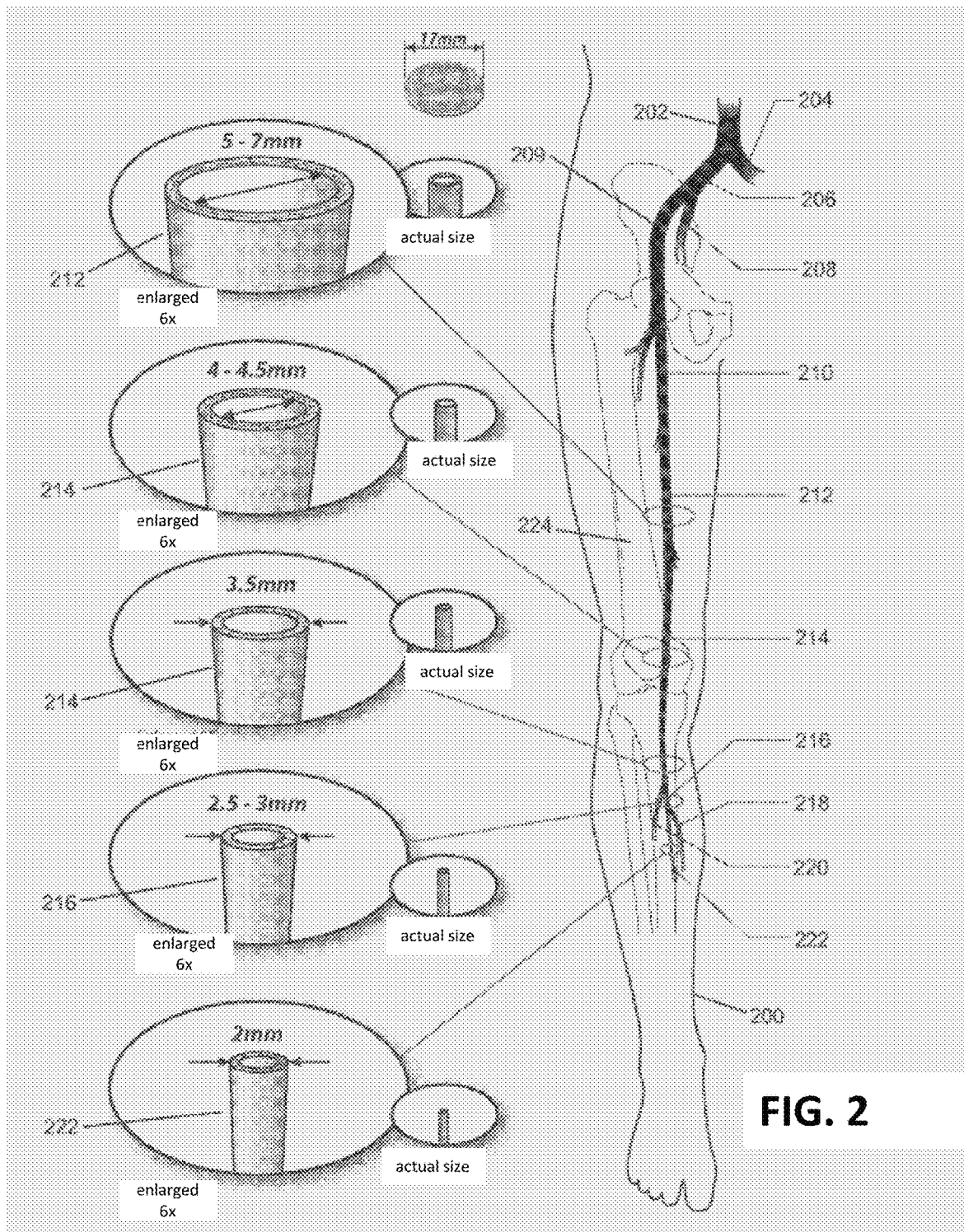
FIG. 2 depicts a diagrammatic anatomic view showing the major arteries of a right leg and typical variations in diameter of the various arteries.

One of the clinical challenges of atherectomy arises from the native anatomy of certain peripheral regions where atherectomy is indicated (for example, in the leg). Accordingly, the following is a descriptive of the leg anatomy for perspective of certain uses of atherectomy devices of the invention. FIG. 2 shows the anatomy of major arteries of a leg (200) (the right leg is shown for the purpose of illustration). Also shown there is the abdominal aorta (202), the left iliac artery (204), the right iliac artery (206), the internal iliac artery (208), the external iliac artery (209), the common femoral artery (210), the superficial femoral artery (212), the popliteal artery (214), the tibioperoneal trunk (216), the posterior tibial artery (218), the anterior tibial artery (220), and the peroneal artery (222). The diameters of the peripheral arteries of the leg generally taper from larger to smaller in the direction of arterial blood flow from above the knee to below the knee.

The abdominal aorta (202) is the largest artery in the body, and its diameter can range from 19 to 25 mm (about 0.75 to about 1 inch). The abdominal aorta successively branches or divides numerous times between the proximal and distal regions of the legs. Each successive branch or division may reduce the diameter of the arteries in the direction of arterial blood flow from the heart to the feet, and the tortuousity of the path generally increases.

The first branching is at the groin, into the left (204) and right (206) common iliac arteries. In the left leg, the left common iliac artery (204) branches into the internal (208) and external (209) iliac arteries. Near the head of the femur bone (224), the external iliac artery (209) becomes the common femoral artery (210) or "CFA". The CFA further connects to the superficial femoral artery (212) or "SFA". The SFA connects to the popliteal artery (214), which runs behind the flexible region of the knee. Above the knee, the SFA generally has a diameter of about 5 to 7 mm, or about 0.2 to 0.25 inch. Traversing distally below the knee (toward the feet), the popliteal artery (214) may further reduce in diameter to about 4 to 4.5 mm (0.157 inch to 0.177 inch), and then further to about 3.5 mm (0.137 inch). Traversing further distally, the popliteal artery (214) eventually branches again into the anterior tibial artery (220) and the tibioperoneal trunk (216), resulting in a further reduction in diameter to about 3.0 mm to 2.5 mm (0.118 inch to 0.098 inch). Traversing further distally, the tibioperoneal trunk further subdivides into the posterior tibial (218) and peroneal (222) arteries, further reducing diameter to about 2.0 mm (0.078 inch). Overall, the diameters of the peripheral arteries of the leg vary typically from about 2 mm (below the knee) to about 7 mm (above the knee).

Atherectomy devices are usually introduced into the vasculature though an iliac artery by either an ipsilateral (i.e., same side) or a contralateral (i.e., opposite side) approach, and typically advanced under fluoroscopic radiographic image guidance through the CFA and into the SFA. Currently, nearly all intravascular atherectomy cases are performed in the SFA, however, in a majority of these cases, potentially treatable atherosclerosis exists on multiple levels of the peripheral arteries, both above and below the knee. Accordingly, the devices and methods described here may be helpful in reaching these potential atherectomy sites.

Figures 3A, 3B:
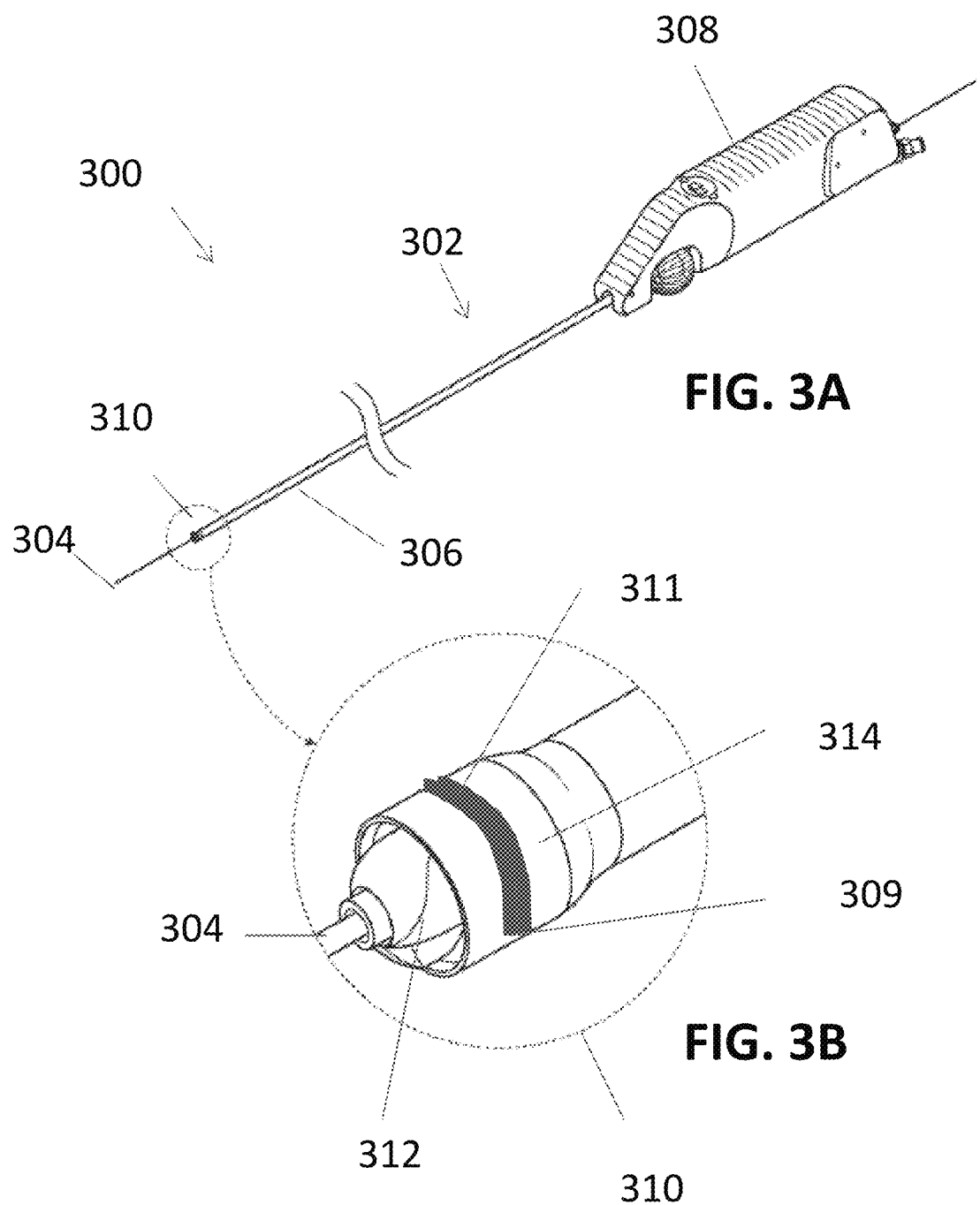
FIG. 3A depicts a perspective view of an illustrative variation of an atherectomy system as described here.
FIG. 3B shows an enlarged perspective view of a distal portion of the atherectomy system shown in FIG. 3A.

FIGS. 3A and 3B illustrate an atherectomy system of the invention, according to certain embodiments. As shown there, the atherectomy system (300) may include an intravascular atherectomy apparatus (302) and a guide wire (304) over which the atherectomy apparatus (302) may be deployed. The guide wire (304) is preferably silicon-coated or non-coated (bare), or otherwise free of a PTFE coating. It should be appreciated, however, that in some variations the atherectomy systems described here may comprise a guide wire that includes a PTFE coating, or that does not include a guide wire at all. In certain embodiments, the guidewire may be a sensing guidewire. For example, the guidewire may be configured to measure functional parameters, such as flow, pressure, temperature, etc. Exemplary functional measurement devices suitable for use in practicing the invention include FloWire Doppler Guidewire and the ComboWire XT Guidewire by Volcano Corporation.

Figures 4A, 4B:
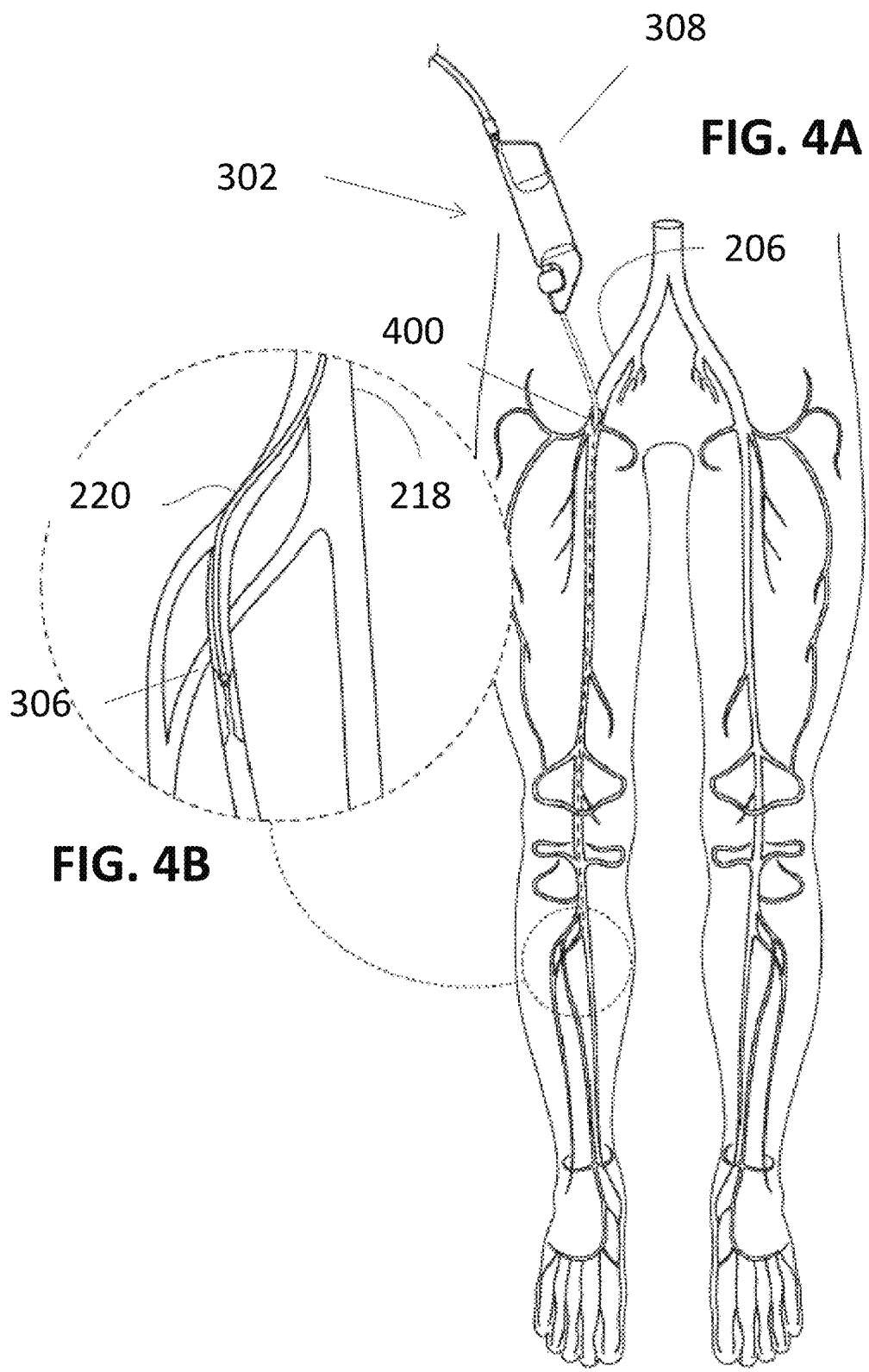

The atherectomy apparatus (302) generally includes an elongated catheter body (306) having a central axis. The catheter body (306) may be sized and configured to be advanced over the guide wire (304) in a blood vessel from an external percutaneous access site. The access approach can be ipsilateral or contralateral, and down to the targeted region. For example, FIGS. 4A and 4B depict views of the anatomy of a patient with a distal portion of the atherectomy apparatus (302) advanced using an ipsilateral approach to a target region in the anterior tibial artery (220). As shown there, the atherectomy apparatus (302) may be introduced into an access site (400) in the right iliac artery (400). Conversely, FIGS. 4C and 4D depict views of the anatomy of a patient with a distal portion of the atherectomy apparatus (302) advanced in a contralateral approach. As shown there, a distal portion of the atherectomy apparatus (302) may be advanced through an access site (404) in the left iliac artery (204), across the iliac bifurcation, and down to the targeted site (in these figures, the targeted site is shown as a branch of the profunda artery (406). In order to follow the intravascular path from the access site to the target region, the catheter body (306) should possess physical and mechanical properties to allow the catheter body (306) to follow the guide wire through a bending, often tortuous intravascular path, as will be described in more detail below.

The atherectomy apparatus (302) may also include a handle (308) is coupled to the proximal (i.e., closest to the caregiver) end of the catheter body (306). The handle may be sized and configured to be securely held and manipulated by a caregiver outside an intravascular path. The handle may be manipulated from outside the intravascular path near the percutaneous access site, which may allow a caregiver to advance the catheter body through the intravascular path, which, in the leg, generally becomes more tortuous as one proceeds toward the distal regions of the legs (below the knee and toward the feet). Image guidance (e.g., CT, radiographic, in situ visualization carried on board the atherectomy apparatus or otherwise provided, or another suitable guidance modality, or combinations thereof) may be used to aid in advancement or positioning of the atherectomy apparatus (302). The catheter body (306) may be advanced to provide access to a targeted region where fat, cholesterol, and other substances have accumulated on the walls of arteries to form plaques or lesions, which will also in general be referred to as "occlusive materials."

The atherectomy apparatus (302) may further comprise a cutter assembly (310) at the distal end (e.g. farthest from the handle) end of the catheter body. Generally, the cutter assembly may act to cut and capture the occlusive material, and thereby remove occlusive material from the artery, which may open the artery to blood flow. In some variations, the cutter assembly (310) may include a rotatable cutter (312) at least partially housed within a concentric cutter housing (314). The cutter (312) may be rotatable within the housing around the central axis of the catheter body. In the variation shown in FIGS. 3A and 3B, the cutter housing (314) may be open at its distal-most end such that the distal-most end of the cutter may project a distance distally from the open housing (314). In some of these variations, when the cutter assembly (310) is deployed in the targeted region where the occlusive materials exist, there may be no structure or component of the atherectomy located in front of (i.e., distal to) the cutter assembly, and thus the first region of the atherectomy apparatus to interact with the plaque is the cutter assembly.

The cutter housing (314) may include an imaging assembly (311) located thereon or embedded therein. The imaging assembly (311) may be used to obtain real-time images of the occlusion (atheroma, plaque, thrombi, or emboli) prior to morcellation with the cutter (312), during morcellation, and after morcellation to observe completeness of the procedure or whether more cutting is necessary to remove the blockage entirely or regain a suitable luminal opening. Suitable imaging assemblies include optical-acoustic imaging apparatus, intravascular ultrasound (IVUS), forward-looking intravascular ultrasound (FLIVUS) or optical coherence tomography (OCT). Preferably, the imaging assembly (311) is an ultrasound-based imaging assembly. The ultrasound imaging assembly may be a phased-array assembly, which includes a plurality of transducer elements. The imaging assembly (311) may located/embedded on a portion of the housing (314). In certain embodiments, the imaging assembly (311) circumscribes the housing (314). In other embodiments, the imaging assembly (311) is located on the catheter body (306) proximal to the housing (314). Imaging assemblies, such as imaging assembly (311), are described in more detail hereinafter.

Figure 5A:
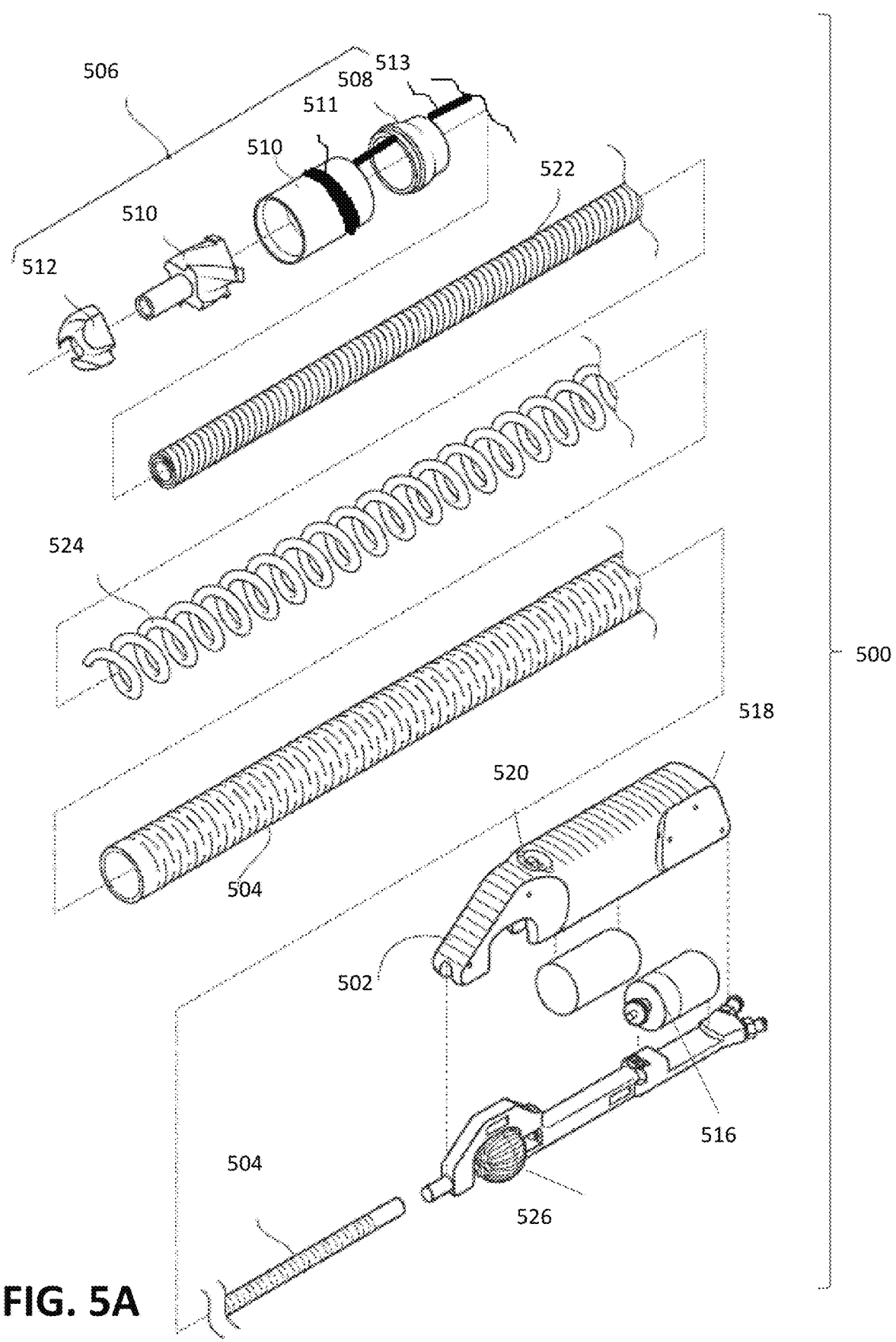
FIG. 5A depicts an exploded perspective view of a variation of the atherectomy systems described here.
Figure 5B:
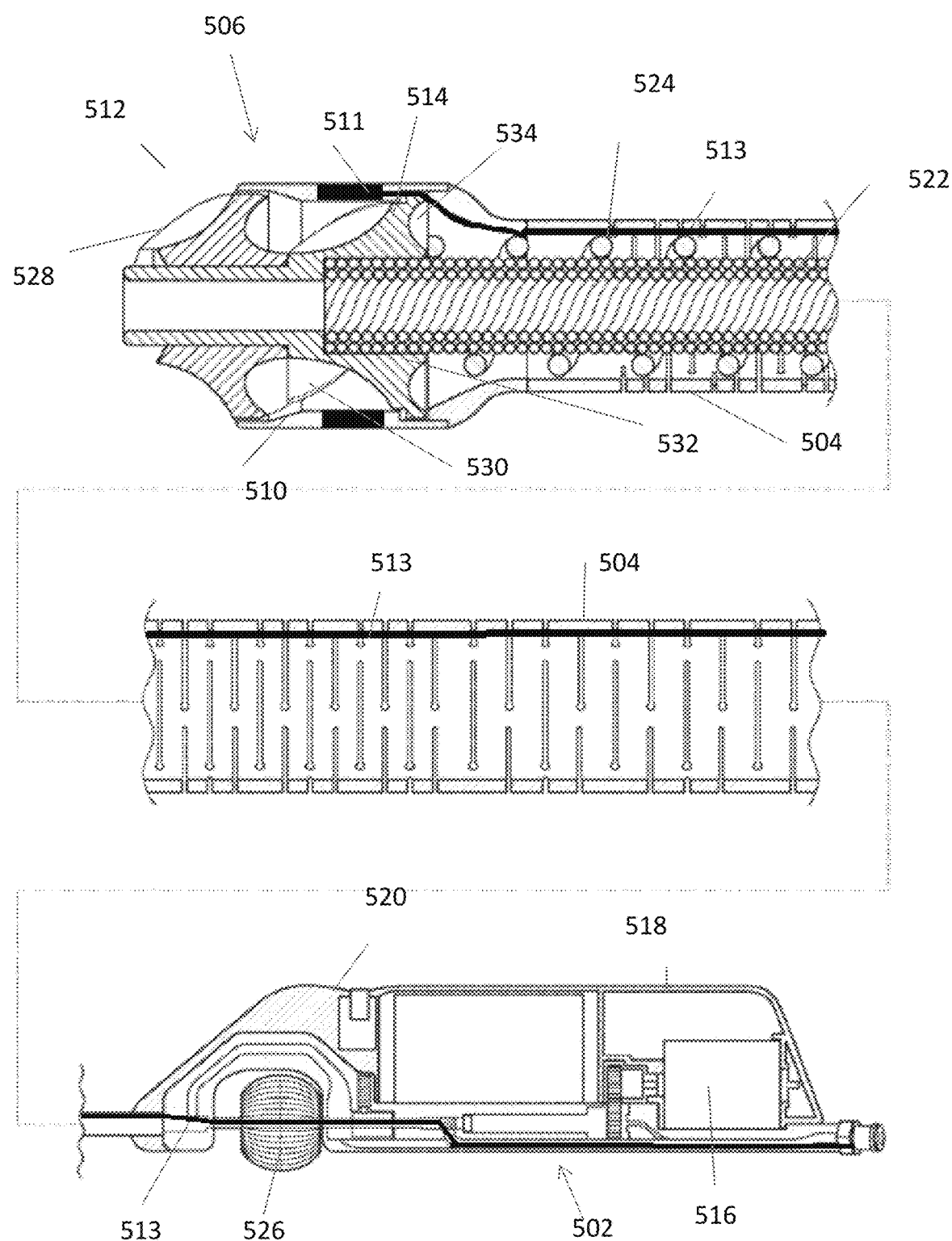
FIG. 5B depicts an assembled cross-sectional side view of the atherectomy system of FIG. 5A.

FIGS. 5A and 5B show a breakdown of an atherectomy apparatus (500) suitable for use with the atherectomy systems described here. As shown there, atherectomy apparatus (500) may comprise a handle (502), a catheter body (504), and a cutter assembly (506), such as described above with respect to FIGS. 3A and 3B. As shown in FIGS. 5A and 5B, the cutter assembly (506) may comprise a ferrule (508), a cutter housing (510), and a cutter including a first cutting element (512) and a second cutting element (514). It should be appreciated that the atherectomy apparatus (500) may comprise any suitable cutter assembly, such as those described in more detail below. The housing 510 may include an imaging assembly 511. The imaging assembly 510 is connected to one or more signal wires (513), which are in turn connected to a signal processing apparatus. The signal wires (513) transmit energy to the imaging assembly 511 to emit imaging signals (such as ultrasound or optical signals) and transmit back signals (back-echos) received from the imaging assembly to a signal processing apparatus and imaging console. The signal wires (513) may run alongside an inner surface of the catheter body (504) to the signal processing apparatus, or the signal wires (513) may be incorporated into the catheter body (504). In certain embodiments, the catheter body (504) may define a separate lumen through which the signal wires (513) may be routed.

The atherectomy apparatus (500) may include a motor (516), which in the embodiment shown in FIGS. 5A and 5B, may be contained within a housing portion (518) of the handle (502). The motor is desirably battery operated, either by use of replaceable batteries, by use of rechargeable batteries, or combinations thereof. A motor controller may desirably provide a consistent supply of power through all operating conditions, including no load through excessive torque and stall conditions. A control switch (520) (e.g., slide switch, pushbutton, and/or potentiometer) may be provided to include an off/on function, and in some instances, one or more of a variety of other control functions, such as ramp up and/or ramp down, and/or variable speed. In some variations, the motor may run at about 12,000 RPM at 6 volts nominal. The operating parameters can be changed by adjusting the gear ratio.

As shown in FIGS. 5A and 5B, a torque shaft (522) may connect the motor (502) to the cutter. Specifically, the motor (502) may rotate the torque shaft (522), which may in turn rotate the cutter within the cutter housing (510) around the central axis of the catheter body. Rotation of the cutter of the cutter assembly (506) may cause the first (512) and/or second (514) cutting elements to cut occlusive material and convey the occlusive materials into the cutter housing (510) (a process also known as "debulking"). Preferably, the cutter assembly (506) captures the cut occlusive materials from the blood without the use of any vacuum aspiration (although it should be appreciated that in some variations, vacuum aspiration may assist conveyance of the cut occlusive material).

Additionally, the atherectomy apparatus (500) may further include an internal conveyor (524) on the torque shaft (522). As occlusive material is conveyed into the cutter housing (510) by the cutter, the conveyor (524) may convey the cut occlusive material further back (proximally) along the catheter body for discharge outside the patient's body. As mentioned above, this conveyance may occur without the use of vacuum aspiration assistance. Mechanical conveyance may complement distal capture. Because it does not require the assistance of vacuum aspiration, mechanical conveyance may minimize the risk of the artery collapsing around the cutter and the associated risk of perforation. Additionally, this conveyance may maximize the removal of tissue and blood components that have been damaged by contact with the cutter assembly.

In further embodiments, the catheter body (504), housing (510) coupled thereto, and imaging assembly (511) located on the housing (510) are configured to rotate. For example, the components may be coupled to a rotary drive shaft to enable rotation. Rotary drive shafts configured to enable rotation of catheter bodies and imaging elements are known in the art. Rotation of these components may serve several purposes. For example, the rotation can act as a means to further dissolve the blockage. In another example, the rotation can assist in moving the broken down blockage particles into the catheter body (504) for removal. Additionally, the rotation can serve to assist in imaging the luminal surfaces of the vessel wall (e.g. the luminal surfaces within intramural space). For example, imaging elements (such as optical coherence tomography and ultrasound imaging elements) capture cross-sectional imaging data obtained during a rotation of the imaging element. In some embodiments, the rotation of the catheter body (504) and associated elements counters the rotation of the torque shaft (522). This counter rotation may increase effectiveness of the internal conveyer (524) in removing the broken down particles.

The individual components of the systems shown in FIGS. 3A, 3B, 5A and 5B are discussed in more detail hereinafter.

B. The Catheter Body

1. Dimensions

For practical purposes, the outer diameter of any section of the catheter body, including the cutter assembly it carries, may be dictated at least partially by the anatomy of the intravascular path and the intended target region. Specifically, it may be desirable to maximize the cutting effectiveness of the cutter assembly by maximizing the diameter of the cutter, while minimizing the potential of puncture or trauma to the vessel. Additionally, the outer diameter of the catheter body/cutter assembly may also be dictated at least partially by the diameter of a guide sheath or introducer selected that may be placed at an access site to allow introduction of the atherectomy apparatus into the vasculature. It may be desirable to select a guide sheath or introducer sized to minimize pain, trauma, and blood loss during use, and to facilitate rapid closure of the access incision after removal, to thereby reduce the incidence of interventional complications.

As mentioned previously, diameters of the peripheral arteries of the leg vary typically from relatively small in regions below the knee (2.0 mm) to relatively large in regions above the knee (7.0 mm). For percutaneous access to the peripheral arteries, clinicians typically use guide sheaths sized from 5F (diagnostic) to 7F (interventional).

Assuming, for example, that a 7 French guide sheath would likely be, from a clinical perspective, the largest selected to access the larger vessels above the knee (4 mm to 7 mm), and allowing for a reasonable clearance tolerance between the catheter body/cutter assembly and the guide sheath, in some instances the outer diameter of the catheter body for introduction through such a guide sheath may be selected to be approximately equal to or less than about 2.4 mm. Assuming that a 5 F guide sheath would likely be, from a clinical perspective, the largest used to access the smaller vessels below the knee (2.5 mm to 3 mm), and allowing for a reasonable clearance tolerance between the catheter body/cutter assembly and the guide sheath, in some instances the outer diameter of the catheter body for introduction through such a guide sheath may be selected to be approximately equal to or less than about 1.8 mm. Assuming that an intermediate 6 French guide sheath would likely be, from a clinical perspective, the largest used to access the intermediate vessels near the knee (3 mm to 4 mm), and allowing for a reasonable clearance tolerance between the catheter body/cutter assembly and the guide sheath, in some instances the outer diameter of the catheter body for introduction through such a guide sheath may be selected to be approximately equal to or less than about 2.2 mm.

It may desirable that the outer diameter of the cutter assembly be maximized, to maximize the overall cutting area of the atherectomy assembly. When the cutter assembly of an atherectomy apparatus is the distal-most component of the apparatus, the cutter assembly may lead the way by cutting through the occlusive materials. With regard to the catheter body, however, there may functional and clinical benefits that arise when the outer diameter of the catheter body is not maximized to match the outer diameter of the cutter assembly. Reducing the diameter of the catheter body relative to the cutter assembly may minimize frictional contact between the catheter body and the vessel wall. This may lessen the force required to advance the catheter body through the vasculature and occlusive material, and may help prevent the catheter body from dragging against or sticking to tissue structures in the vessel, or otherwise impeding the progress of the cutter assembly through the occlusive materials.

For example, it may be desirable that the outer diameter of the catheter body proximal of the cutter assembly be sized smaller than the outer diameter of the cutter assembly. In other instances, it may be desirable that the outer diameter of the catheter body proximal of the cutter assembly be sized equal to or smaller than the outer diameter of the cutter assembly. For example, in the variation of atherectomy apparatus (500) described above with respect to FIGS. 5A and 5B, the catheter body (504) may have an outer diameter less than an outer diameter of the cutter assembly (506).

The reduced diameter of the catheter body may also permit the injection of radiographic contrast material around the catheter body in the guide sheath. For example, an atherectomy apparatus for introduction through a 7F introducer system may have a 2.4 mm diameter cutter assembly and a catheter body having a 2.2 mm diameter. In other variations, an atherectomy apparatus for introduction through a 5F or 6F introducer system may have a 1.8 mm diameter cutter assembly and a catheter body having a 1.6 mm diameter, or a 2.2 mm diameter cutter assembly and a catheter body having a 1.6 mm diameter.

2. Catheter Properties

In addition to the anatomical and clinical considerations that may be used in selecting an outer diameter of a catheter body, the catheter body may also desirably possess certain physical and mechanical properties, such as those described immediately below, which may enhance the function of the catheter body to support and guide passage of the cutter assembly through the intravascular path and the occlusive materials.

(i) Column Stiffness (Pushability)

One potentially desirable property for the catheter body includes column stiffness. Expressed in units of inch/foot-pounds, column stiffness is the capability of the catheter body to withstand an axial load or compression while resisting bending. Column stiffness can be measured and characterized in conventional ways, and may be referred to as "pushability" herein. Generally, a higher column stiffness is desirable, and may allow the catheter body to transmit a higher axial force (compression) applied at the handle to the cutter assembly without buckling. Accordingly, it may be desirable that the catheter body possess column stiffness sufficient to push the cutter assembly over the guide wire without buckling. A column stiffness of 0.050 inches/lbf or greater may be desirable for the catheter bodies described here.

(ii) Tensile Stiffness (Pullability)

Another potentially desirable property for the catheter body comprises tensile stiffness. Expressed in units of inch/foot-pounds, tensile stiffness is the capability of the catheter body of withstanding tension while being stretched or pulled before the cross section starts to significantly contract (called "necking"). Tensile stiffness can be measured and characterized in conventional ways, and may be referred to as "pullability" herein. Generally, a high tensile stiffness may be desirable, and may allow the catheter body to be pulled proximally along an intravascular path (e.g., to withdraw the cutter assembly) without necking. A tensile stiffness of 0.050 inches/lbf or greater may be desirable for the catheter bodies described here.

(iii) Torsional Stiffness (Torquability)

Another potentially desirable property for the catheter body comprises torsional stiffness. Expressed in degrees/ounce-inch, torsional stiffness is the capability of the catheter body to transmit a rotational load (torque) without untwisting, over-twisting and/or deforming. Torsional stiffness may be measured and characterized in conventional ways, and may be referred to as "torquability" herein. The torsional stiffness may control the capability of the catheter body to transmit a given amount of rotation applied at its proximal end (i.e., the handle) to achieve a comparable amount of rotation at its distal end (i.e, the cutter assembly). A higher torsional stiffness may be desirable, to better allow for rotational transmission along the atherectomy apparatus (i.e., around a guide wire), without twisting or deforming. A torsional stiffness that achieves a 1:1 relationship between rotation applied at the proximal end and the rotation observed at the distal end may be desirable for the catheter bodies described here.

(iv) Bending Stiffness (Trackability)

Another potentially desirable property for the catheter body comprises bending stiffness. Expressed in units of a bend radius (in inches), bending stiffness is the ability of the catheter shaft to bend in response to an applied bending force, without breaking or deforming (i.e., without taking a set). Bending stiffness is an extensive material property that can be measured and characterized in conventional ways, and may be referred to as "trackability" herein. Generally, a lower bending stiffness may be desirable to allow the catheter body to be navigated over a guide wire around sharp bends in the vasculature. A targeted bending stiffness of 0.5 inches (bend radius) or greater at mid-length of the catheter body may be desirable for the catheter bodies described here. If the catheter body includes an active deflection component at its distal end (as will be described in greater detail later), a targeted bending stiffness of 1.0" (bend radius) at the deflectable distal end may be desirable for the catheter bodies described here. A prescribed minimum bend radius also makes it possible to coil the catheter body for packaging without taking a set.

Conventionally, trackability is thought to be inversely related to pushability/pullability and torquability. That is, greater pushability, pullability, and/or torquability in a catheter body may reduce the trackability of the catheter body. However, the catheter bodies described here may balance the pushability, pullability, torquability, and trackability for a given catheter body. The result may be a catheter body that is trackable, yet also possesses the requisite column strength, tensile strength, and torsional stiffness to be sufficiently pushable, pullable and torquable to allow navigation and advancement of a cutter assembly.

The overall trackability of a given catheter body (in terms of its ability to reliably navigate over a guide wire) may be influenced mainly by the physical and mechanical characteristics of the catheter body at its distal end. The pushability, pullability, and torquability may be influenced mainly by the physical and mechanical characteristics of the catheter body proximal to its distal end. That is, the overall configuration of different regions of a catheter body may impart characteristics to the overall length of the catheter body, which may allow for optimization of the overall pushability, pullability, torquability, and trackability of the catheter body.

3. Catheter Body Variations

Generally, the column stiffness, tensile stiffness, torsional stiffness, and bending stiffness for a catheter body may be at least partially determined by its constituent material or materials, the dimensions of catheter body (e.g., the interior diameter, the outer diameter, wall thickness, etc.) and other structural features such as patterning. The catheter bodies may be fabricated from a metal tube (for example, a type 304 stainless steel tube or the like). The dimensions of the tube may depend at least partially on the intended use of the atherectomy apparatus. For example, in some variations the outer diameter of the tube may desirably be about 2.2 mm, while in other variations the outer diameter of the tube may be about 1.6 mm. Additionally or alternatively, the wall thickness of the tube may preferably be about 0.288 mm. Additionally or alternatively, the overall length of the tube may preferably be about 1437 mm (about 56.56 inches).

A metal tube with some or all of the dimensions described immediately above may provide a high degree of pushability, pullability, and torquability, the baseline bending stiffness may limit the trackability of the catheter body given the length of the catheter body. Accordingly, in some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability. In certain embodiments, one or more zones of the catheter body include helical cut patterns, threaded cut patterns, spiral cut patterns, or brickwork cut patterns. A catheter body having any of the cut patterns can be lined or jacketed with a polymeric material, and further may be treated to produce hydrophilic, hydrophobic, or drug binding (heparin, antimicrobial) properties.

4. Catheter Body Rotation

As discussed above, the catheter body 504 (along with the housing and imaging assembly) may be configured for rotation. In certain embodiments, the catheter body 504 is coupled to a rotary drive shaft that drives the rotation of the catheter body 504. In other variations, the catheter body can be coupled to a post on the handle that is sized and configured to rotate in response to rotation of a control knob. For example, the atherectomy apparatus (500) described above with respect to FIGS. 5A and 5B may comprise a rotation knob (526). Rotation of the knob may apply torque to the catheter body to selectively rotate the cutter assembly. An indexing mechanism can be provided to provide stepwise control, with tactile and/or audible feedback, so that the caregiver maintains knowledge of the rotational position of the cutter assembly without taking their eye off the radiographic or otherwise provided in-situ image.

It is also possible to apply torque to the catheter body by rotating the handle itself. Selective rotation of the cutter assembly can thus be finely controlled by a combination of control knob manipulation and handle twisting.

C. The Cutter Assembly

As mentioned above, the atherectomy device may comprise a cutter assembly. The cutter assembly may comprise a ferrule, a cutter housing, and a cutter comprising at least one cutter element. In variations in which the cutter assembly comprises a ferrule, the cutter assembly may be joined to the distal end of the catheter body by the ferrule. In certain embodiments, the cutter assembly further includes an imaging assembly associated with the cutter housing.

1. The Cutter Housing

As mentioned previously, the cutter assembly may include a housing in which a cutter rotates. It may be desirable to maximize the outer diameter of the cutter assembly (and with it, the cutter housing) to maximize the cutting area that may be cut by the cutter assembly. The size of the cutter assembly may be limited depending on the intended intravascular path and the region targeted for treatment, to help reduce the likelihood that the cutter assembly will cut or otherwise damage the vessel wall.

In some of the variations described here, a cutter assembly sized for introduction through a 7 French guide sheath may have an outer diameter of about 2.4 mm (which, in some variations, may be larger than the outer diameter of a companion catheter body, as described in more detail above). A cutter assembly having such an outer diameter may be used, for example, for access to the larger vessels above the knee (e.g., vessels between about 4 mm and about 7 mm). In other variations described here, a cutter assembly sized for introduction through a 5 or 6 French guide sheath may have an outer diameter of about 1.8 mm to about 2.2 mm (which, in some variations, may be larger than the outer diameter of a companion catheter body, as described in more detail above). A cutter assembly having such an outer diameter may be used, for example, for access to the smaller vessels at or below the knee (e.g., vessels between about 2.5 mm and about 4 mm).

The housing may or may not be dynamic (i.e., able to rotate relative to the catheter body). In variations where the housing is dynamic, the housing may be configured to rotate at the same speed or at a different speed than the cutter elements. Additionally, the cutter housing may be dynamically driven to rotate in the same direction or in a counter direction relative to the cutter.

The housing may include one or more imaging assemblies. The imaging assembly may be located on or embedded within the housing. The imaging assembly may cover a portion of the housing, and preferably the imaging assembly circumscribes the housing. The imaging assembly is connected to one or more signal wires that run the length of the atherectomy device.

The leading edge of the cutter housing, which defines the periphery of the distal opening through which the cutter projects, may desirably be rounded and does not present a sharp distal edge. In these variations, a rounded distal housing may reduce the possibility that the peripheral edges of the housing catch on the wall of the guide sheath during introduction therethrough. Additionally, a rounded distal edge may also tend to glance off tissue without grabbing or catching on the tissue, which may minimize the resistance felt by the atherectomy apparatus during advancement. It should be appreciated that in some variations the cutter housing may have a sharp or beveled distal edge. In some of these variations, the cutter housing may have an inner bevel. In other variations, the cutter housing may have an outer bevel.

In some variations, the outside diameter of the cutter may be less than the inside diameter of the cutter housing to create a desired cutting gap between the two. A larger gap may produce a larger cutting volume, but too large of a gap may permit tissue to enter the cutter housing while bypassing the cutter. Representative dimensions will be described in more detail later. In other variations, the outside diameter of a portion of the cutter may be greater than or equal to the diameter of the cutter housing. In these variations, the cutter may cut a larger diameter of tissue, which may reduce the likelihood that the cutter housing rubs against tissue during advancement while cutting, thereby facilitating advancement of the device.

2. The Torque Shaft

The cutter is coupled and rotatable by the torque shaft. The torque shaft may be, in turn, driven by the motor in the handle. The torque shaft may be fabricated from any suitable material, preferably one or more materials that may be consistent with the pushability, pullability, torquability, and trackability of the catheter body, as described above. For example, the torque shaft may comprise a metal braid and/or one or more metal coils, and one or more portions of the torque shaft embedded in a polymer, e.g., PEBAX, polyurethane, polyethylene, fluoropolymers, parylene, polyimide, PEEK, and/or PET. In some variations, the torque shaft may be made from a rigid material such as plastic, rendered flexible by incorporation of a spiral relief or groove.

In some variations (such as the torque shaft depicted above with respect to FIGS. 3A, 3B, 5A and 5B), the torque shaft may comprises a flexible wire coil wound about a central lumen. The central lumen may be sized to accommodate the passage of a guide wire therethrough. The flexible wire coil may preferably be wound in the same direction as the intended direction of rotation of the torque shaft, which may cause the coil to open up if torsional resistance to rotation is encountered (as opposed to clamping down, which may cause the torque shaft to lock on to a guide wire positioned in the central lumen).

Generally, the torque shaft may be coupled to a cutter of a cutter assembly at or near the distal end of the torque shaft, and may be attached to the motor (e.g., by gearing) at or near the proximal end of the torque shaft. In some variations (such as the atherectomy apparatus depicted in FIGS. 3A, 3B, 5A and 5B), the cutter assembly may include a central lumen that may communicate with the central lumen/guide wire lumen of the torque shaft.

3. The Geometry of the Cutting Elements

As mentioned above, in some variations, the cutter of a cutter assembly may comprise multiple cutting elements. For example, in the variation of the atherectomy apparatus (500) described above with respect to FIGS. 5A and 5B, the cutter assembly (506) may comprise a cutter having first (512) and second (514) cutting elements. As shown there, the first cutting element (512) may be positioned distally of second cutting element (514). The first cutting element (512) may comprise one or more cutting edges (528) which may at least partially project beyond the distal end of the cutter housing (510). In some variations, at least a portion of the first cutting element (512) may have a diameter greater than or equal to the diameter of the cutter housing (510). The second cutting element (514) may be at least partially housed within the cutter housing (510), and may comprise one or more cutting edges (530). As shown in FIG. 5B, the cutting edges (530) of the second cutting element (514) may be entirely enclosed within the cutter housing (510). Generally, the first (512) and second (514) cutting elements may be physically coupled together (e.g., by adhesives or welding) for rotation in unison.

The torque shaft may couple to a journal (532) in the second cutting element. When the first (512) and second (514) cutting elements are physically coupled together, the torque shaft may rotate both the first cutting element and second cutting element in unison. A proximal flange (534) on the second cutting element (514) may be seated within a relieved proximal groove (536) in the cutter housing (510). The relieved proximal groove (536) may serve as an axial retainer for the first (512) and second (514) cutting elements within the cutter housing.

(i) The First Cutting Element

FIGS. 6A-6D depict an illustrative variation of a first cutting element (800) suitable for use with the cutter assemblies described here. In some variations, the first cutting element (800) may be machined from a hard metallic material (e.g., 440C stainless steel) and may have a generally hemispherical configuration that includes at least one helical flute (802) (shown there as a right-hand twist, although it should be appreciated that the at least one helical flute (802) may have a left-hand twist). While shown in FIGS. 6A-6D as having two helical flutes (802), it should be appreciated that the first cutting element (800) may comprise any suitable number of helical flutes (802) (e.g., one, two, three, four, or more helical flutes). Each cutting flute may form a cutting blade (803) having a cutting edge (804).

The first cutting element may be machined to shape the structure of the helical flutes (802) within the desired hemispherical geometry. When supported in an extended, distally projecting relationship relative to the cutter housing (e.g., by virtue of the connection to a second cutting element, as described in more detail above), the hemispherical, fluted geometry may be sized and configured to optimize the capability of the cutting blade or blades to cut through and capture occlusive materials, while minimizing the risk of the cutting blade or blades grabbing or digging into tissue, wrapping tissue, and otherwise causing the motor to stall and overload.

The geometry of each flute may be purposely shaped for the above-mentioned purposes, and the flute geometry may be characterized with reference to a combination of angles (or ranges of angles), comprising a rake angle, a relief angle, a flute angle, and a helix angle. Additionally, while shown in FIGS. 6A-6D as having a hemispherical outer profile, it should be appreciated that the front cutting element may any external profile, such as an egg-shaped outer profile.

(a) Rake Angle

For each flute, the rake angle (806) (best shown in FIG. 6C) can be defined as the angle measured between (i) a radius (808) drawn from the rotational axis of the cutting blade (810) to the most radially distant edge (804) of the blade (803) and (ii) a tangent (810) drawn from the inner face of that blade (803). The rake angle may describe the angle of the cutting edge (804) relative to the material to be cut.

In some variations, each flute of the first cutting element may possess a positive rake angle (i.e., the inner face of the cutting blade slants inward or back from the cutting edge). The positive rake angle of each flute is preferably large, and in some instances may be between greater than about 20 degrees. In some of these variations, the rake angle is preferably greater than about 40 degrees. In some of these variations, the rake angle may be between about 60 degrees and 80 degrees (referred herein as a "high" rake angle). In some variations, the rake angle may be between 65 degrees and 75 degrees. In some variations, the rake angle may be about 70 degrees.

Generally, a device having a positive high rake angle may be well suited for cutting occlusive materials having less calcium, which may have a fibrous, fleshy, and/or rubbery consistency. The rubbery consistency may cause conventional cutters to deflect away from these materials, causing conventional devices to lose trackability, but a high rake angle helps a cutter slice into this tissue while minimizing deflection of the cutter. Conventional cutter machining techniques generally cannot produce a positive high rake angle cutter, and these cutters generally have a small rake angle (less than about 15 degrees). Additionally, a larger rake angle may decrease the structural integrity of a cutter, which may the cutter more likely to chip or break during use. The cutters described here, however, may allow for the benefits of high rake angle cutting while reducing the risk of cutter malfunction.

The rake angle of the cutter may be modified depending on the nature of the tissue to be cut. For example, a cutter assembly intended to cut hard, calcified occlusive materials having a higher calcium content, may be configured to have a negative rake angle (i.e., the inner face of the cutting blade may slant outward or forward of the cutting edge), which may be well suited for grinding or smashing hardened occlusive materials. It should be appreciated that a given cutting element can be machined to incorporate cutting blades having both positive and negative rake angles or otherwise include combination of both cutting and grinding surfaces. For example, in some variations a cutter may comprise a first cutting element having a plurality of helical flutes, wherein at least one flute has a cutting edge having a positive rake angle and at least one flute has a cutting edge having a negative rake angle. In some of these variations, the helical flutes having cutting edges having a positive rake angle may have a positive rake angle greater than about 20 degrees (e.g., greater than about 40 degrees or about 70°+/− 10°).

Figure 6A:
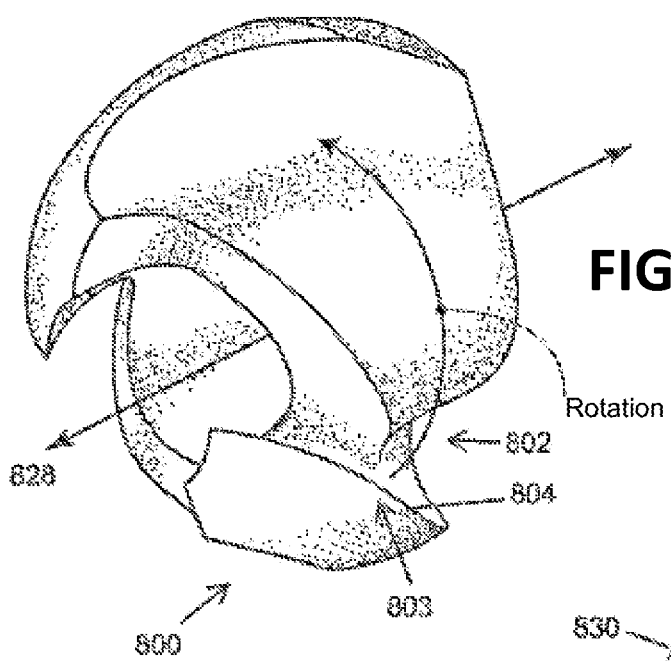
FIGS. 6A and 6B depict a perspective distal view and a side view, respectively, of a variation of a representative cutting element as described here.
Figure 6B:
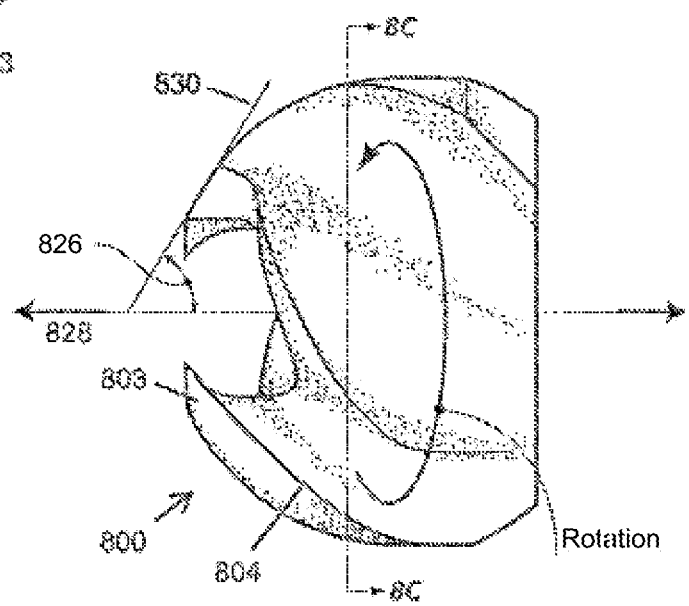
Figure 6C:
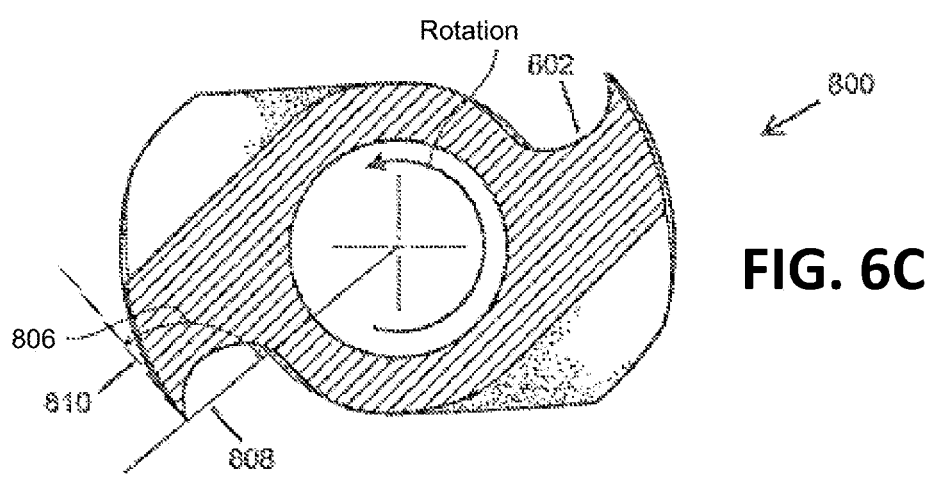
FIG. 6C is a cross-sectional view of the representative cutting element taken along line 8C-8C in FIG. 6B.
Figure 6D:
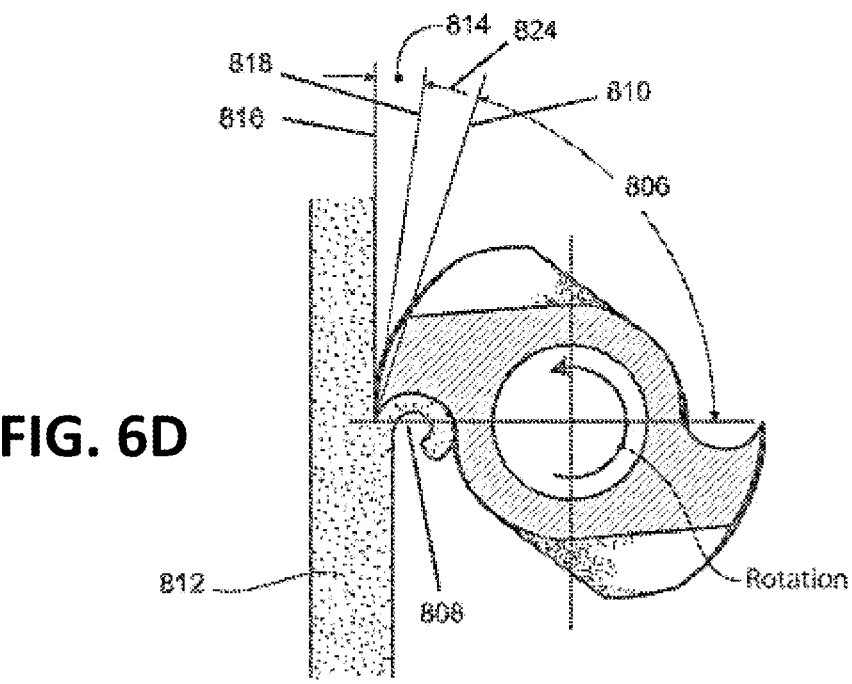
FIG. 6D is a cross-sectional view of the representative cutting element, like that shown in FIG. 6C, cutting into occlusive materials.

In the variation of first cutting element (800) shown in FIGS. 6A-6D, the formation of a flute having a large, positive rake angle (e.g., 70° . . . +−0.10°.) may create a cutting blade having an enlarged concave inner face. The enlarged concave inner face may define a trough- or scoop-shaped blade that may efficiently slice through the occlusive materials (812) as shown in FIG. 6D. The large, positive (high) rake angle and resulting enlarged concave inner face of the cutting blade may reduce cutting forces and power requirements for the first cutting element (800) and may remove large volume of occlusive materials with each pass of the cutting blade.

(b) Relief Angle

For each flute, the relief angle (814) can be defined as the angle measured between (i) the tangent (816) drawn from the most radially distant edge (804) of the cutting blade (803) from radius (808) and (ii) the tangent (818) drawn along the outer face of the blade (803). The relief angle generally spans the gap between the cutting edge (804) and the occlusive material (812) surface to be cut (such as shown in FIG. 6D). Generally, a smaller relief angle may form a more tangential interface with a tissue surface during cutting, which may reduce the likelihood that a cutting edge may snag or otherwise catch on tissue during cutting. A larger relief angle may provide more aggressive cutting.

Generally, the relief angle is preferably a small angle less than or equal to about 10°. (e.g., between about 0° and about 10°). In some of these variations, the relief angle may be about 0°. In some variations, it may be preferable to have a rake angle of about 70 degrees and a relief angle of about 0 degrees. In other variations, a helical flute may have a rake angle of about 60 degrees and a relief angle of about 10 degrees. The formation of a flute with a small relief angle may create a cutting edge (804) that may make aggressive contact with the occlusive materials (812) such as shown in FIG. 6D. Together with a large positive (high) rake angle, a small relief angle may lead to highly efficient cutting and capture of occlusive materials at the distal end of the cutter assembly, minimizing residue and embolization.

(c) Flute Angle

For each flute, the flute angle (824) can be defined in terms of a relationship with the rake angle and the relief angle, as follows: Flute Angle=90°−(Rake Angle)−(Relief Angle)

The magnitude of the flute angle is an indication of how thick and sharp the cutting edge is. Given that, in a preferred embodiment, the rake angle may be in a range between about 60°, and 80°; the relief angle may be in a range between of about 0° and 10°, the flute angle may be in range between about 0° and about 30°. Maximizing the rake angle and minimizing the relief angle to achieve efficient cutting conditions may result in a cutter geometry having a reduced flute angle. Accordingly, it may be desirable that the first cutting element be machined from a hard metallic material to include at a cutting edge that is a sharp as possible. In some variations, is may also be desirable to coat the cutting blade with a biocompatible, highly lubricious material with a low coefficient of friction (preferably no greater than 0.5) to help keep the cutting blade sharp during use. In these variations, coating materials such as titanium nitride or diamond-like carbon (DLC) may be used.

(d) Helix Angle

In the variation of the first cutting element (800) shown in FIGS. 6A-6D, each flute (802) of the first cutting element (800) may comprise a helical cut. The helix angle (826) may be defined as the angle between (i) the rotational axis (828) of the cutting blade (803) and (ii) a tangent (830) drawn along the inner face the cutting blade (803). The magnitude of the helix angle is indicative of the capability of the cutting blade to transport cut occlusive material proximally along the cutting blade and into the housing.

In some variations, each flute (802) of the first cutting element (800) may have a helix angle (802) between about 30° and 60°. A helix angle below 30° may increase the likelihood the first cutting element (800) may overload with occlusive material and stall, while a helix angle above 60° may diminish the cutting efficiency of the first cutting element (800).

Figure 8A:
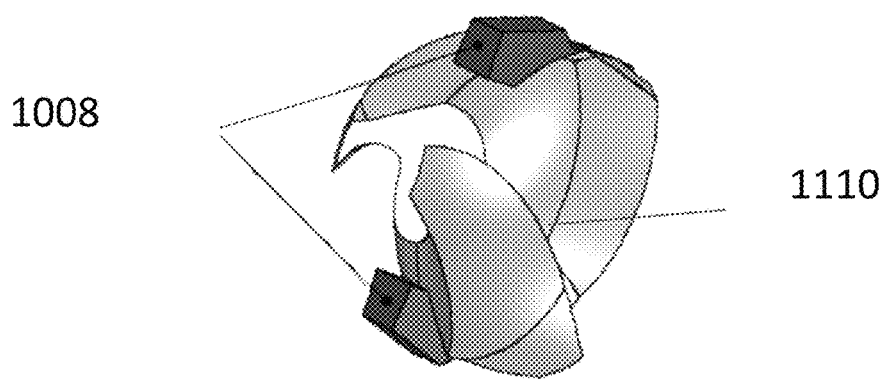
FIGS. 8A-8C depict various views of a cutting element, according to certain embodiments.
Figure 8B:
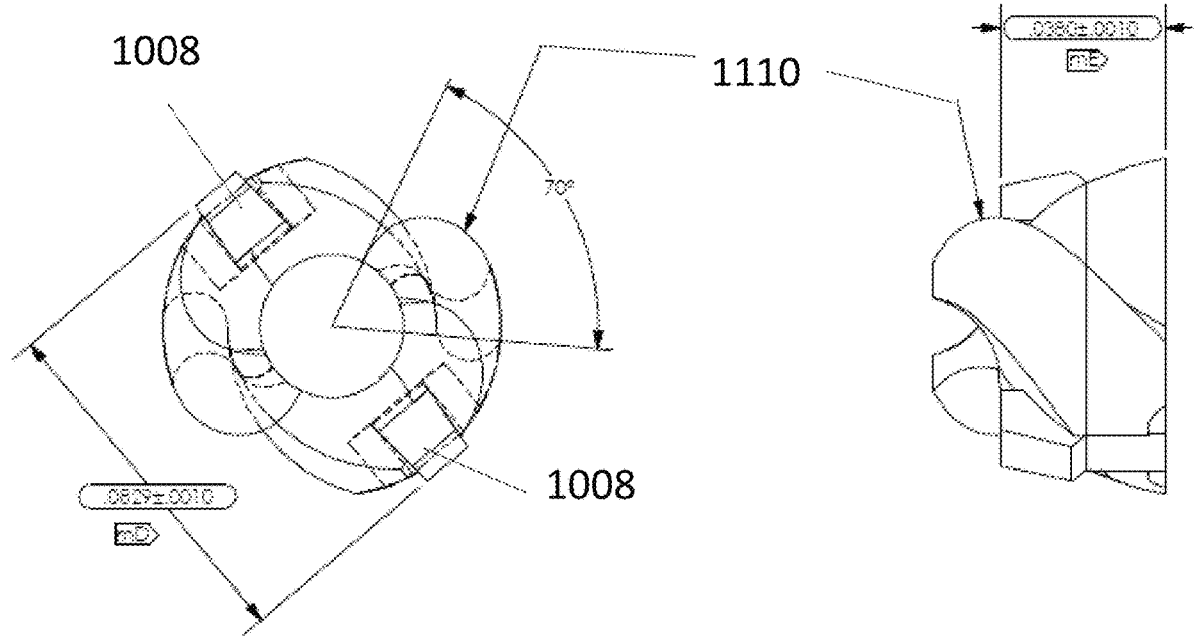
Figure 8C:
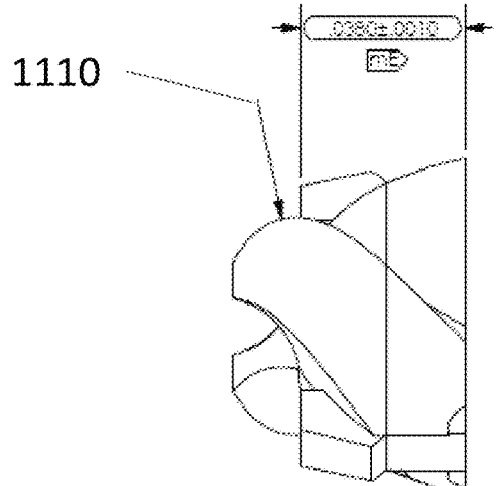

FIGS. 8A-8C illustrate the first cutting element according other embodiments. As shown in FIG. 8A-8C, the cutting element may include one or more blades 1110, one or more blunt crushing elements 1008, or both. The one or more blades 1110 may be designed with the angle geometries discussed above. The blades 1110 are designed to cut through the occlusion as the cutting element is rotated. The crushing elements 1008 are designed to deliver a crushing blow to the occlusion. That is, the crushing elements 1008 are designed to deliver a blow or sudden impact to the occlusion that further breaks up the occlusion beyond what is possible with the blades 1110 alone. Particularly, the crushing elements 1008 are useful in breaking through fibrous plaque and highly organized thrombi. The crushing elements 1008 are preferably blunt and substantially rectangular in shape. In certain embodiments, the crushing elements 1008 form a zero rake angle or a negative rake angle (as opposed to the positive rake angle of the blades 1110). The negative rake angle may range from at least 1, 5, 10, 15, 20, 25 30 degrees or more. Although, the crushing elements 1008 may include other shapes, such as spherical, triangular, cylindrical, hexagonal, etc. While the body of a crushing element is generally blunt, the edges of the crushing element may be sharp to also assist in cutting through the occlusion. The one or more crushing elements 1008 may be located between the blades 1110 (as shown in FIGS. 8A-8C). In certain embodiments, the crushing elements 1008 are formed from a different material than the rest of the cutting element. The crushing elements 1008 are ideally formed from carbide metal, such as titanium carbide.

(ii) The Second Cutting Element

As mentioned above, the cutter assembly may comprise a second cutting element. For example, in the variation of atherectomy apparatus (500) shown in FIGS. 5A and 5B, the cutter assembly (506) may comprise a second cutting element (514). In variations that include a second cutting element, the second cutting element may be machined from a hard metallic material (e.g., 17-4 stainless) to include helical cutting flutes. The cutting flutes may be configured to have the same rake angle, relief angle, flute angle, and helix angle as the flutes of the first cutting element. In some variations, the above-mentioned geometries of the first and second cutting elements may be identical, except that the second cutting element has more flutes than the first cutting element. In some of these variations, the second cutting element may have double the number of flutes of the first cutting element; that is, four flutes are shown.

In some variations, the second cutting element is machined to include a hollow stem that fits within a center journal of the first cutting element. For example, in the variation of the atherectomy apparatus shown in FIGS. 5A and 5B, the second cutting element (514) may include a stem (538) around which the first cutting element (512) can be placed. For example, FIG. 9 shows a perspective view of cutter assembly (506), in which the first (512) and second (514) cutting elements may be joined together (e.g., by adhesive or welding) in a rotationally aligned condition. In the aligned condition, two opposing cutting flutes (540) of the second cutting element (514) may be rotationally aligned with the two opposing cutting flutes (542) of the first cutting element (512). Their geometries may be matched during machining, and may act to cut and conveyed occlusive material proximally by the first cutting element into the housing and further convey the occlusive material more proximally into contact with the additional cutting blades of the second cutting element.

(iii) Two-Stage Cutting Action

Figure 7:
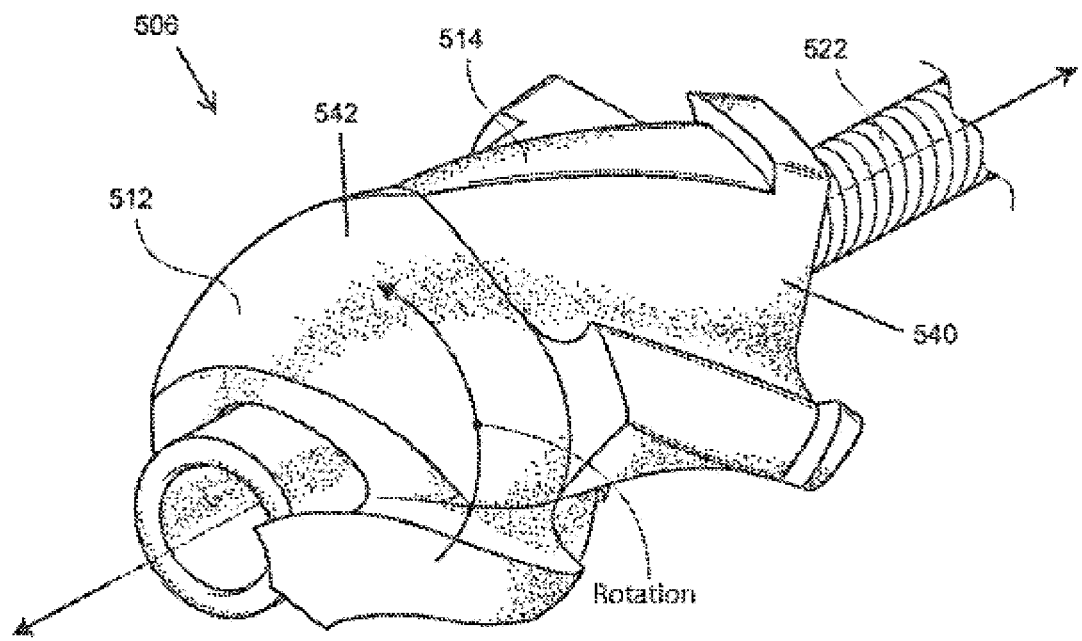
FIG. 7 depicts a distal perspective view of a variation of a cutter comprising first and second cutting elements.

The cutter assembly (506) shown in FIG. 7 may provide a two-stage cutting action. Generally, the first cutting element (512) may cut occlusive material and convey the material to the second cutting element (514). The second cutting element (514) may further cut or macerate the occlusive materials into smaller particles. During both cutting actions, the occlusive materials may be continuously captured within the housing and conveyed proximally away from the targeted intravascular site. When the first and second cutter elements rotate, the helical cutting surfaces formed by the flutes may cut occlusive materials in the blood vessel and may convey the occlusive material from the blood vessel into the housing through the action of the helical flutes, and may do so without the assistance of any vacuum aspiration.

D. Mechanical Removal of Occlusive Materials

Figure 9A:
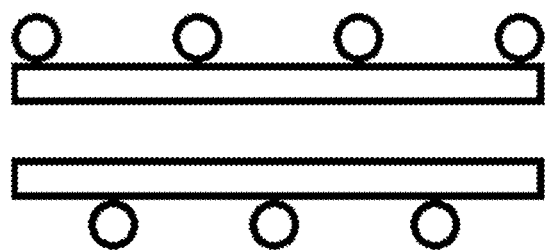
FIGS. 9A-9B illustrates cross-sections of the internal conveying member, according to certain embodiments.
Figure 9B:
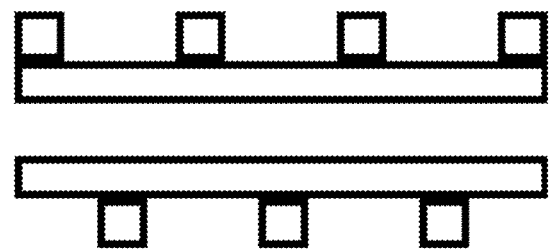
Figure 10:
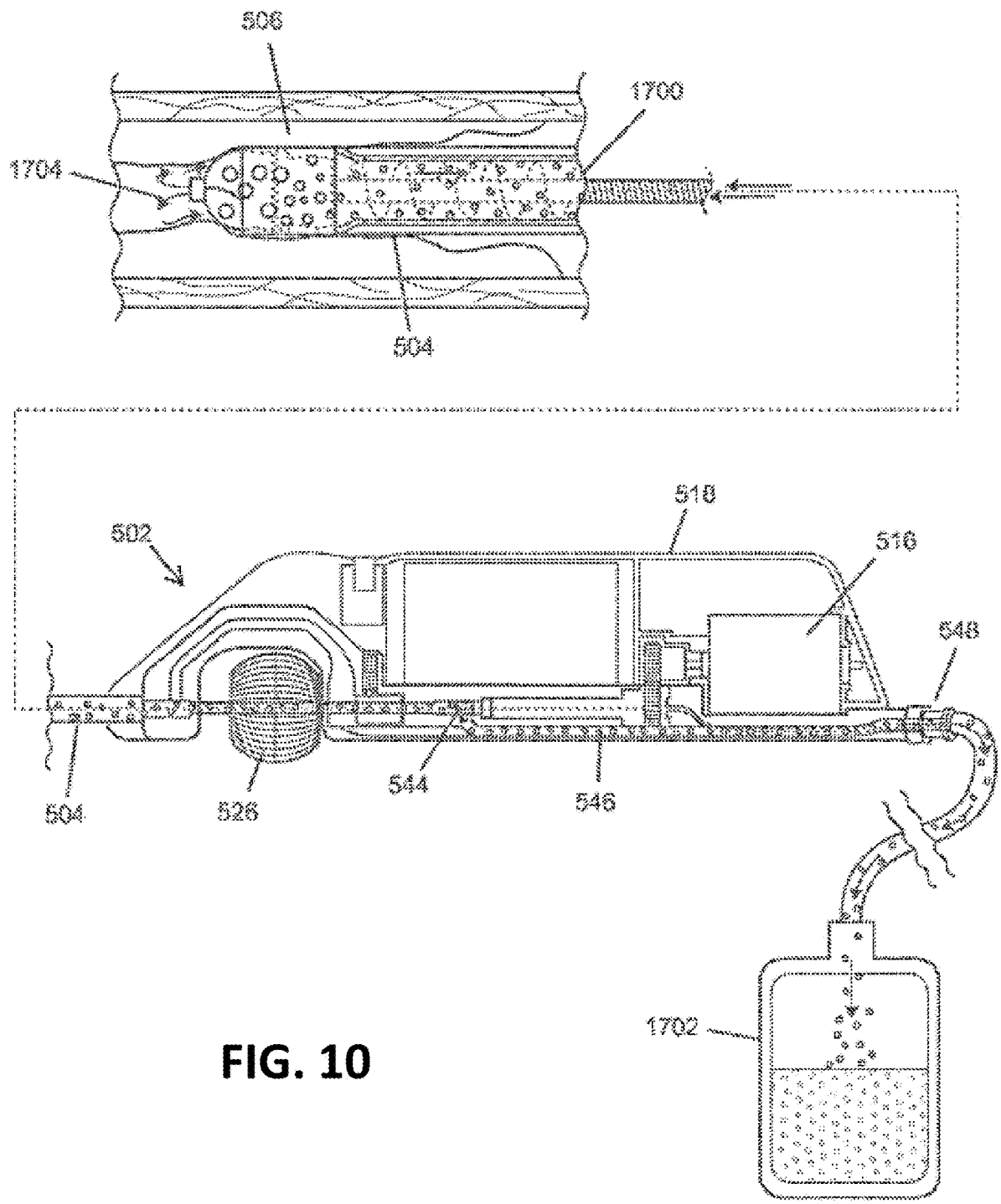
FIG. 10 illustrates removal of occlusion through atherectomy devices describe herein.

As mentioned above, in some variations of the atherectomy apparatuses described here, the atherectomy apparatus includes an internal conveying member. For example, the variation of atherectomy apparatus (500) shown in FIGS. 5A and 5B may comprise an internal conveyor (524). In variations that include an internal conveying member, the internal conveying member may comprises a wire helically wound about the torque shaft in a direction common with the helical cutting surfaces of the cutter assembly. The cross-section of the internal conveyer member may be substantially circular or rectangular in shape. FIG. 9A illustrates the internal conveying member with a circular cross-section and FIG. 9B illustrates the internal conveying member with a rectangular cross-section. A rectangular cross-section may increase the amount of contact between the conveyer and the internal surface of the catheter body, thereby increasing the conveying member's ability to move blockage particles down the length of the catheter. When a cutter assembly cuts and captures occlusive material (e.g., when the helical flutes of a first and/or second cutting element conveys cut and captured occlusive materials to the conveying member), the conveying member may rotate in common with a torque shaft to convey the cut and captures occlusive materials it receives from the cutter assembly further back (proximally) along the catheter body into the handle. For example, FIG. 10 shows the variation of atherectomy apparatus (500) described above with respect to FIGS. 5A and 5B conveying and transferring occlusive material (1700) proximally through the apparatus.

The occlusive materials carried back by the conveying element into the handle may be transferred into a discharge passage within the handle. A transfer propeller communicating with the discharge passage may be coupled to the torque shaft to rotate in common with the torque shaft, and may act to pump the cut, captured, and conveyed occlusive materials into the discharge passage. The discharge passage may include an external coupler (e.g., a leur connector) to couple the discharge passage to an external waste container. The cut and captured occlusive materials may be conveyed into the waste receptacle, and may be done so without need for vacuum aspiration. For example, as shown in FIG. 10, atherectomy apparatus (500) may comprise a transfer propeller (544), a discharge passage (546), and an external coupler (548), which may be connected to an external waste container (1702) as just described.

In some instances, it may be desirable to convey saline or another biocompatible fluid down the catheter body for mixing with occlusive material within the cutter assembly. Mixing the fluid with the occlusive materials may form a slurry, which may reduce the viscosity of the materials cut, captured, and conveyed from the vessel by the atherectomy apparatus. This may reduce the load imposed on the cutter assembly and facilitate the transfer of materials into the waste receptacle. As shown in FIG. 10, the atherectomy apparatus (500) may convey a fluid (1704) from the distal end of the device. In some variations, the fluid (1704) may be conveyed through an internal/guide wire lumen within the torque shaft (522).

II. Deflectable Atherectomy Systems and Apparatuses

A. Overview

In some variations, the atherectomy systems described here may comprise an atherectomy apparatus configured to selectively dynamically deflect at its distal end (e.g., near a cutter assembly). For example, FIGS. 11A-11D show one variation of an atherectomy apparatus (1800) comprising a handle (1802), a catheter body (1804), and cutter assembly (1806). These elements may include any of the features previously described. As will be described in greater detail, the catheter body (1804) may be configured to dynamically deflect at its distal end (where the cutter assembly (1806) is carried) relative the central axis of the proximal catheter body (1804), as shown in FIG. 11C. This deflection may occur without axial advancement of the atherectomy apparatus. Additionally, the atherectomy apparatus (1800) may be configured to rotate the distal end of the apparatus while deflected about the central axis of the proximal catheter body (1804) to sweep the cutter assembly (1806) in an arc (1808) around the central axis, as shown in FIG. 11D. The ability of the atherectomy apparatus (1800) to sweep may allow for the cutter assembly to cut occlusive materials in a region larger than the outside diameter of the cutter assembly, as will be described in more detail below.

The atherectomy apparatus (1800) may be used in an atherectomy system including a guide wire (1810), and may be introduced into a blood vessel from an external percutaneous access site such as described previously with respect in FIGS. 4A-4D. The handle (1802) may be sized and configured to be securely held and manipulated by a caregiver outside an intravascular path in a manner previously described to advance the catheter along an intravascular. Image guidance (e.g., CT, radiographic, or guidance mechanisms, or combinations thereof), may be used to aid the caregiver's manipulation.

Figure 11A:
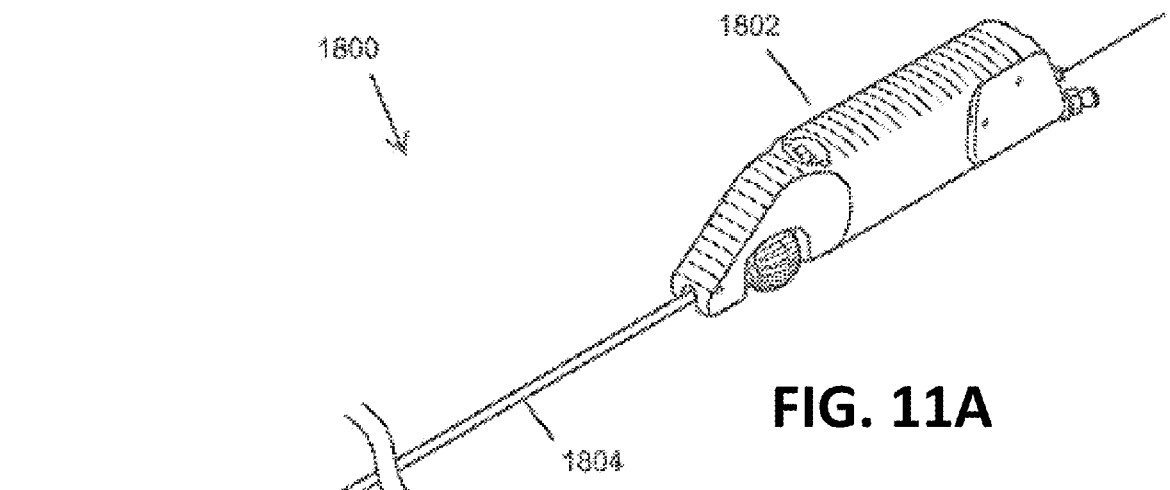
FIG. 11A depicts a perspective view of a variation of the atherectomy systems described here.
Figure 11B:
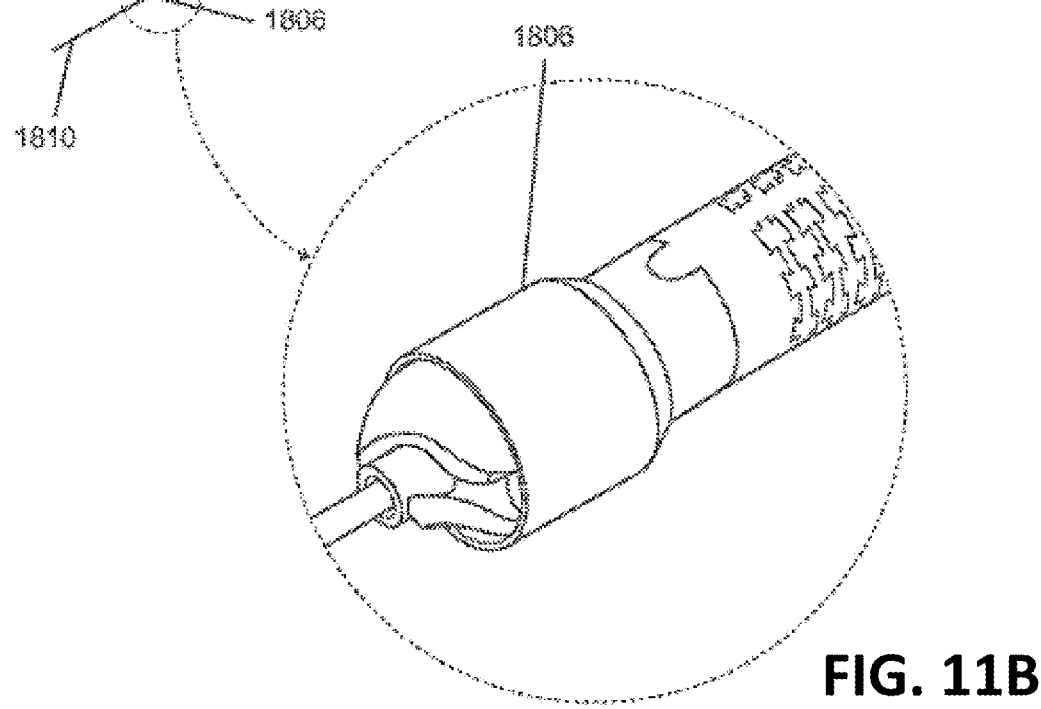
FIG. 11B is an enlarged perspective view of a distal portion of the atherectomy system shown in FIG. 11A.
Figure 11C:
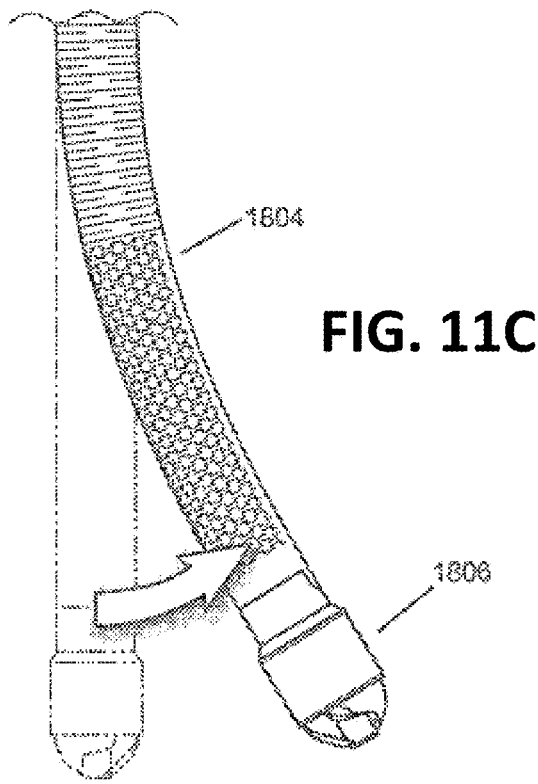
FIGS. 11C and 11D depict different manners in which the atherectomy system as shown in FIG. 11A may be manipulated.
Figure 11D:
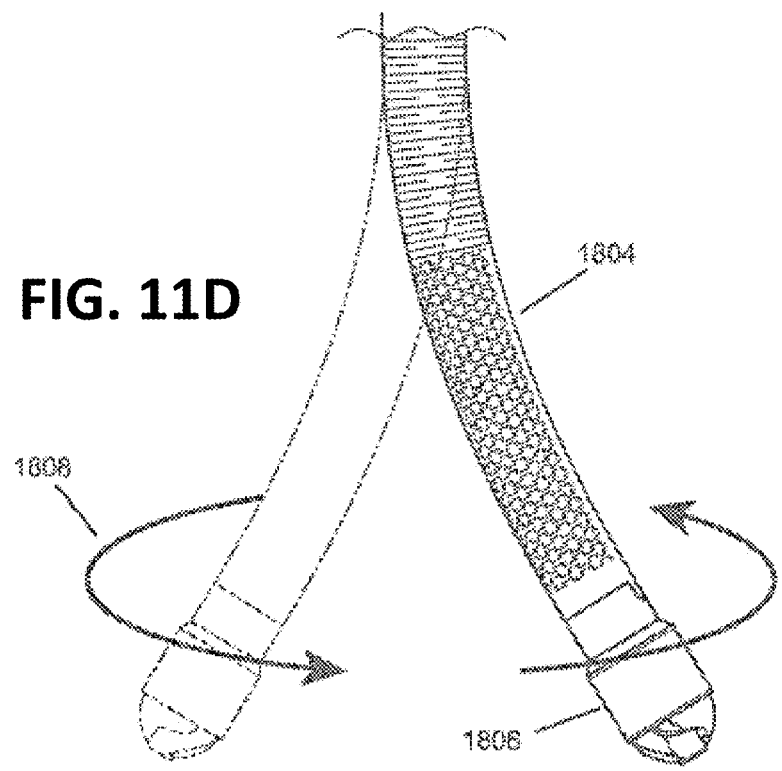

FIGS. 11A and 11B depict a variation of an atherectomy apparatus (2000) configured for use with the atherectomy systems described here. As shown there, atherectomy apparatus (2000) may comprise a handle (2002), a catheter assembly (2004), and a cutter assembly (2006). As shown there, the cutter assembly (2006) may comprise a ferrule (2008), a cutter housing (2010), a first cutting element (2012), and a second cutting element (2014). The cutting assemblies may have any elements or combination of elements as described in more detail above. For example, the cutter housing (2010), first cutting element (2012), and second cutting element (2014) may have any of the elements and dimensions previously described. In some variations, the first and second cutting elements may each comprise one or more helical cutting flutes having a rake angle between about 60 degrees and 80 degrees, a rake angle less than or equal to 10 degrees (in some of these variations, about 0 degrees), a flute angle between about 30 degrees and about 0 degrees, and a helix angle between about 30 degrees and about 60 degrees.

Figure 12A:
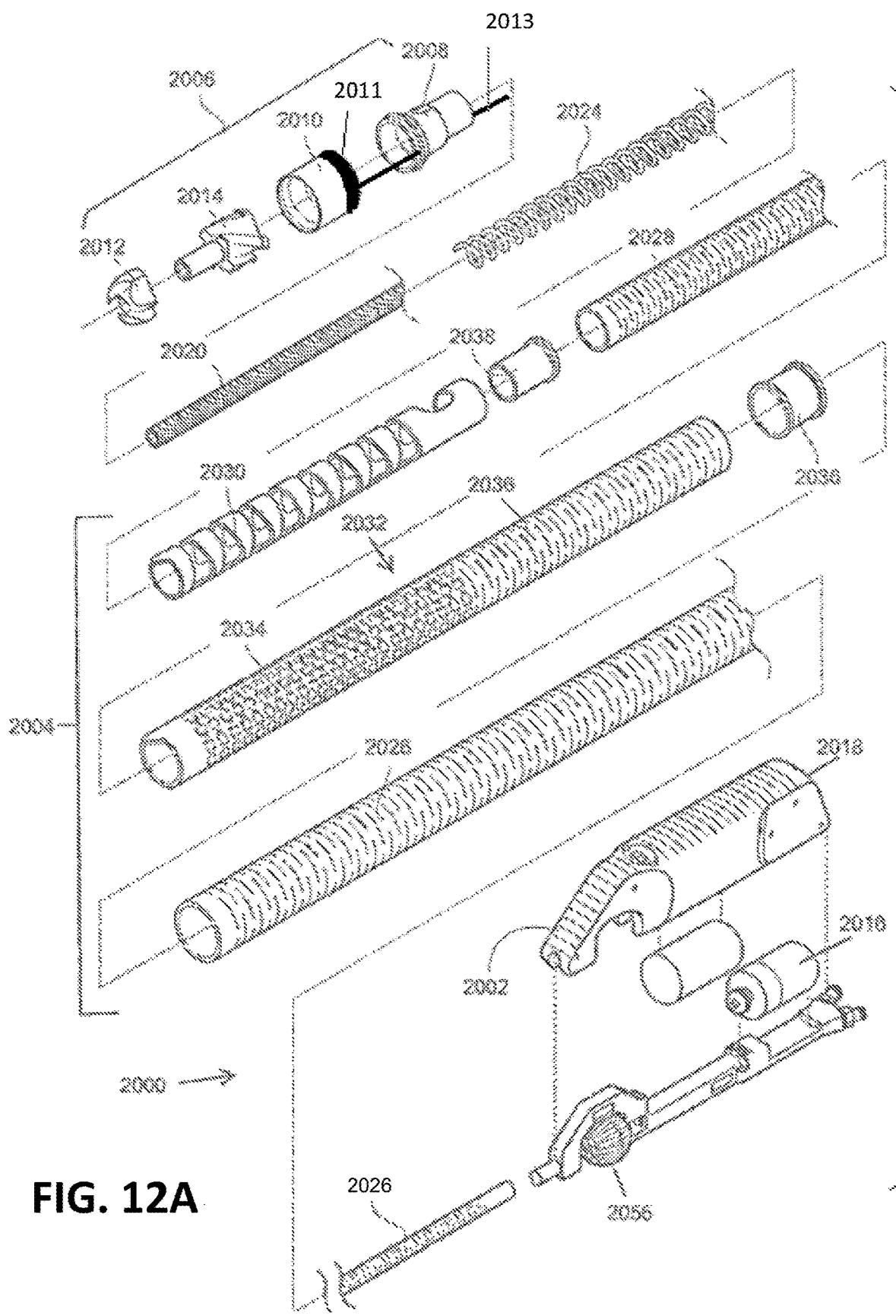
FIG. 12A is an exploded perspective view of a variation of the atherectomy systems described here.
Figure 12B:
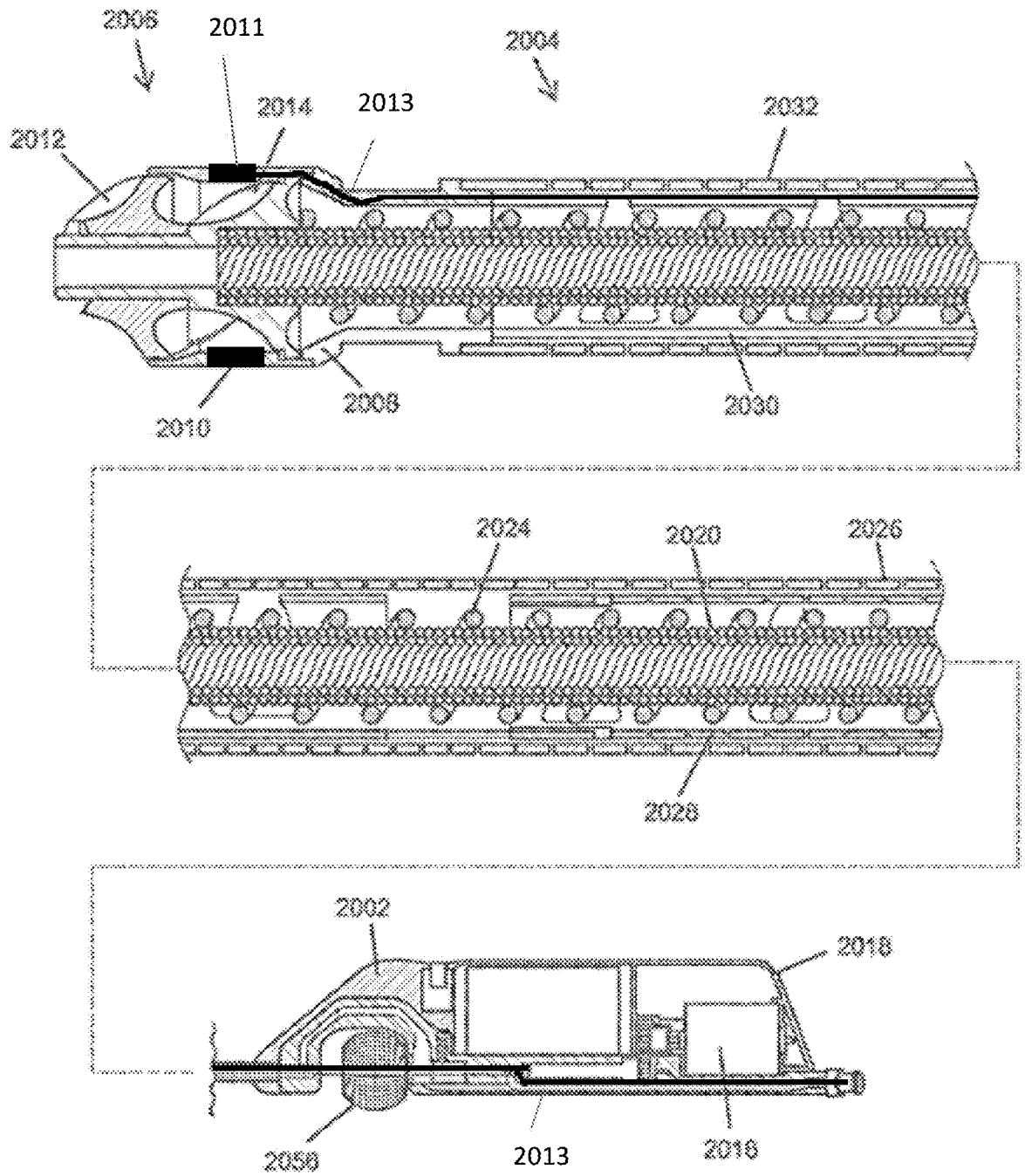
FIG. 12B depicts an assembled cross-sectional side view of the atherectomy system shown in FIG. 12A.

Also shown in FIGS. 12A and 12B, the atherectomy apparatus (2000) may further comprise a drive motor (2016), which in some variations may be contained within a housing (2018) of the handle (2002). Also shown there is a torque shaft (2020) which may be coupled by gearing to the motor (2016) at a proximal end of the torque shaft (2020) and coupled to the second cutting element (2014) at a distal end of the torque shaft (2020). The torque shaft rotates the first (2012) and second (2014) cutting elements relative to the cutting assembly, such as described in more detail above. When the cutter rotates, it may cut and convey occlusive materials into the cutter housing (2010), and may do so without the use of any vacuum aspiration.

The cutter housing (2010) may include an imaging assembly (2011) located thereon or embedded therein. The imaging assembly (2011) may be used to obtain real-time images of the occlusion (atheroma, plaque, thrombi, or emboli) prior to morcellation with the cutter (2012), during morcellation, and after morcellation to observe completeness of the procedure or whether more cutting is necessary to remove the blockage entirely or regain a suitable luminal opening. Suitable imaging assemblies include optical-acoustic imaging apparatus, intravascular ultrasound (IVUS), forward-looking intravascular ultrasound (FLIVUS) or optical coherence tomography (OCT). Preferably, the imaging assembly (2011) is an ultrasound-based imaging assembly. The ultrasound imaging assembly may be a phased-array assembly, which includes a plurality of transducer elements. The imaging assembly (2011) may located/embedded on a portion of the housing (2010). In certain embodiments, the imaging assembly (2011) circumscribes the housing (314). In other embodiments, the imaging assembly (2011) is located on the catheter assembly (2032) proximal to the housing (2010). The imaging assembly 2011 is connected to one or more signal wires (2013), which are in turn connected to a signal processing apparatus. The signal wires (2013) transmit energy to the imaging assembly 2011 to emit imaging signals (such as ultrasound or optical signals) and transmit back signals (back-echos) received from the imaging assembly to a signal processing apparatus and imaging console. The signal wires (2011) may run alongside an inner surface of the catheter assembly (2036) to the signal processing apparatus, or the signal wires (2011) may be incorporated into the catheter assembly (2036). In certain embodiments, the catheter assembly (2036) may define a separate lumen through which the signal wires (2013) may be routed.

The atherectomy apparatus (2000) may also further comprise an internal conveyor (2024), which may convey the occlusive materials from the cutter housing (2010) further back (proximally) along the catheter body for discharge outside the patient's body. In these variations, there may be no need for use of a vacuum pump.

The individual components of the systems shown in FIGS. 11 and 12 are discussed in more detail hereinafter.

B. The Catheter Body

1. Overview

As mentioned previously, the atherectomy apparatus (2000) may comprise a catheter assembly (2004). The catheter assembly may have any suitable dimensions, such as described in more detail above. For example, in some variations, the catheter assembly (2004) may have an outer diameter less than or equal to the outer diameter of the cutter assembly (2006), In some of these variations, the catheter assembly (2004) may have an outer diameter less than the outer diameter of the cutter assembly (2006). In some of these variations, a cutter assembly may have an outer diameter of 2.4 mm, and the catheter assembly may have an outer diameter of 2.2 mm. The catheter assembly may be configured to balance the column stiffness (pushability), tensile stiffness (pullability), torsional stiffness (torquability), and bending stiffness (trackability) of the catheter assembly, such as described in more detail below.

The catheter assembly (2004) may comprise an outer catheter shaft (2026), an inner catheter shaft (2028), and a sweep tube assembly comprising an inner sweep tube (2030) and an outer sweep tube (2032).

2. The Outer Catheter Shaft

The outer catheter shaft (2026) may be formed in any suitable manner. For example, the outer catheter shaft (2026) may be formed from a metal tube (e.g., a 304 stainless steel tube). The outer catheter shaft (2026) may have any suitable dimensions. For example, in some variations it may be desirable for the outer catheter shaft (2026) to be formed from a tube having an outside diameter of about 2.2 mm, a wall thickness of about 0.288 mm, and a length of about 1347 mm (53.03 inches).

As discussed previously, a metal tube with some or all of the dimensions described immediately above may provide a high degree of pushability, pullability, and torquability, the baseline bending stiffness may limit the trackability of the catheter body given the length of the catheter body. Accordingly, in some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability.

The catheter bodies may have any number of zones/regions having different cut patterns (or in some zones, no cut pattern at all). In certain embodiments, one or more zones of the catheter body include helical cut patterns, threaded cut patterns, spiral cut patterns, or brickwork cut patterns. As mentioned above, the outer catheter shaft can be lined or jacketed with a polymeric material, and further may be treated to produce hydrophilic, hydrophobic, or drug binding (heparin, antimicrobial) properties.

3. The Sweep Tube Assembly

As mentioned above, the catheter assembly (2004) shown above in FIGS. 12A and 12B may comprise a sweep assembly comprising an outer sweep tube (2032) and an inner sweep tube (2030). The outer sweep tube (2032) may be connected to the distal end of the outer catheter shaft (2026) (e.g., via coupler (2036)) at a proximal end of the outer sweep tube (2032), and may be connected to the cutter assembly (2006) at a distal end of the outer sweep tube (2032).

As will be described in greater detail below, within the outer sweep tube (2032), the inner catheter shaft (2028) may be coupled to the proximal end of the inner sweep tube (2030) (e.g., via inner coupler (2038)). Sliding the inner catheter shaft (2028) in a distal direction may cause the inner sweep tube (2030) to preferentially bend away from the center axis, thereby preferentially deflecting the cutter assembly toward a side wall of the vessel.

(a) The Outer Sweep Tube

The outer sweep tube (2032) may be formed from a metal tube (e.g., 304 stainless steel). As mentioned above the outer sweep tube (2032) may have a distal sweep portion (2034) and a proximal post portion (2036). The distal sweep portion (2034) and the proximal post portion (2036) may be formed from a single tube, or may be formed separately and joined (e.g., by spot welding). The distal sweep portion (2034) and proximal post portion (2036) may have any suitable lengths. In some variations, the distal sweep portion (2034) may have an axial length of about 0.450 inches and the proximal post portion (2036) may have an axial length of about 0.400 inches.

In some variations, the proximal post portion (2036) may comprise a cut pattern (such as one or more of the patterns described above) to decrease the bending stiffness of the proximal post portion (2036). In some of these variations, the proximal post portion (2036) may comprise a 135° cut/45° uncut alternating brickwork pattern with a pitch of about 0.12 inches. The highly flexible nature of such a two-post pattern may provide a flexible transition between the outer catheter body (2026) and the distal sweep portion (2034) of the outer sweep tube (2032).

The distal sweep portion (2034), conversely, may be configured to impart a preferential bending property in a predetermined direction. In some variations, the distal sweep portion (2034) may comprise a pattern of closed, interlocking cuts (which may be laser cut). In the variation shown in FIGS. 12A, 12B, the closed, interlocking cuts (2038) may extend in rows that extend around a majority of the circumference (e.g., 350°) of the outer sweep tube, which may leaving a spine (2040) of uncut material (e.g., about 10° of uncut material) that extends axially along the distal sweep portion (2034).

In some variations, the interlocking cuts (2038) may comprise chamfered dovetail cuts. These cuts may provide a plurality of rows of material extending from the spine (2040). The rows (which may have an maximum uncut length of 0.25" each) may be separated by about 0.007 inches of chamfered, dovetail cuts (at 67.4°). The interlocking cuts (2038) may have any number of dovetail cuts (e.g., twelve dovetail cuts along the circumference in each row). In some variations, the distal sweep portion (2034) may include with a proximal uncut region (adjacent the proximal post portion (2036), which may be about 0.01 inches in length) and a distal uncut region (adjacent the cutter assembly, which may be between about 0.025 inches to 0.35 inches). Additionally, in some variations a tab (2042) of uncut material may extend beyond the distal end in alignment with the spine (2040), which may form an outer tube alignment key, as will be described in greater detail later.

The laser-formed pattern of closed, interlocking cuts as just described may resist bending in any direction except in the direction of the spine (2040). When a bending force is applied, the interlocking cuts open to permit the bending to occur in the direction of the spine. Bending force in any other direction may be resisted, as the interlocking cuts are closed to resist bending in these directions.

(b) The Inner Sweep Tube

The inner sweep tube (2030) may be fabricated from a metal tube formed (e.g., nitinol). The inner sweep tube (2030) may extend axially within the outer sweep tube (2032) and may have any suitable dimensions. For example, in some variations the inner sweep tube (2030) may have an outer diameter of about 0.068 inches and an inner diameter of about 0.058 inches, and may have a total axial length of about 0.700 inches.+−0.0.005 inches.

Figure 13A:
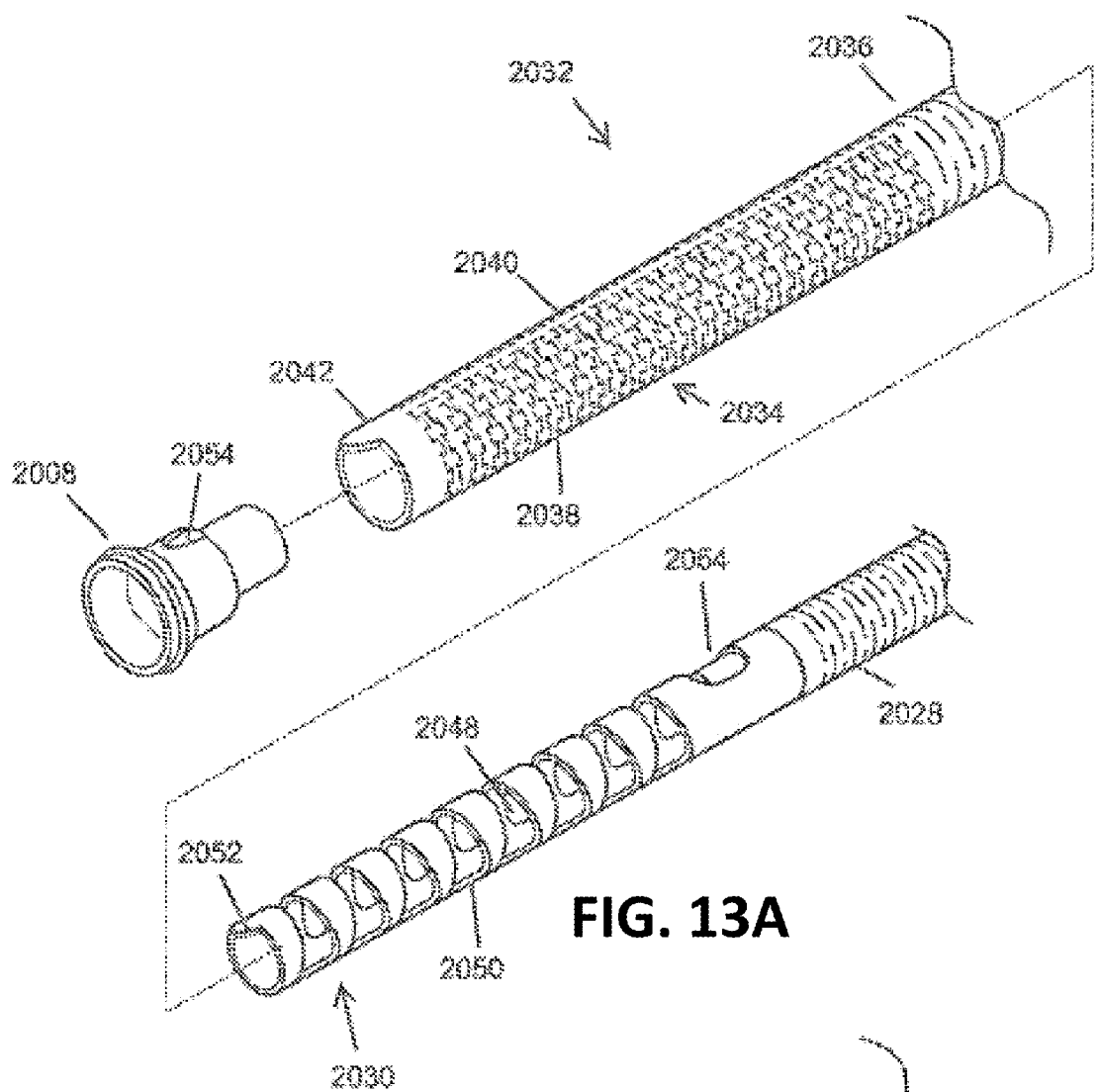
FIG. 13A is an exploded perspective view of a portion of the atherectomy system of FIGS. 12A and 12B.

In some variations, the baseline bending stiffness of the inner sweep tube (2030) may be reduced to impart a preferential bending property in a predetermined direction. In some of these variations, preferential bending may be created using a pattern of open, dovetail cuts (2048). In the variation shown in FIGS. 12A, 12B, and 13A-13D, the closed, open, dovetail cuts (2048) may extend around a majority of the circumference (e.g., 350°) of the inner sweep tube (2030), which may leaving a spine (2050) of uncut material (e.g., about 10° of uncut material) that extends axially along the inner sweep tube (2030). As shown in FIG. 13A, the spine (2040) of the outer sweep tube (2032) and the spine (2050) of the inner sweep tube (2030) may be aligned such that spine (2040) and spine (2050) may be positioned on opposite sides of the catheter assembly.

The dovetail cuts (2048) may have any suitable dimensions. For example, in some variations the dovetail cuts (2048) each extend about 0.55 inches along the axis of the inner sweep tube (2030), and may include any number of dovetail cuts (2048). In some of these variations, the inner sweep tube (2030) may comprise eight dovetail cuts, which may extend about 0.60" along the spine (2050). Additionally, in some variations a tab (2052) of uncut material may extend beyond the distal end in alignment with the spine (2050), which may form an inner tube alignment key, as will be described in greater detail later.

The laser-formed pattern of open cuts as just described permit preferential bending in the direction of the open cuts, away from the spine, until the open cuts come together and interfere in a distal to proximal succession. When a bending force is applied thereto, the open cuts may permit bending, but, as the bending continues, may resist bending as cuts close and interfere. A preformed bending radius may thereby be built into the inner sweep tube.

Figure 13B:
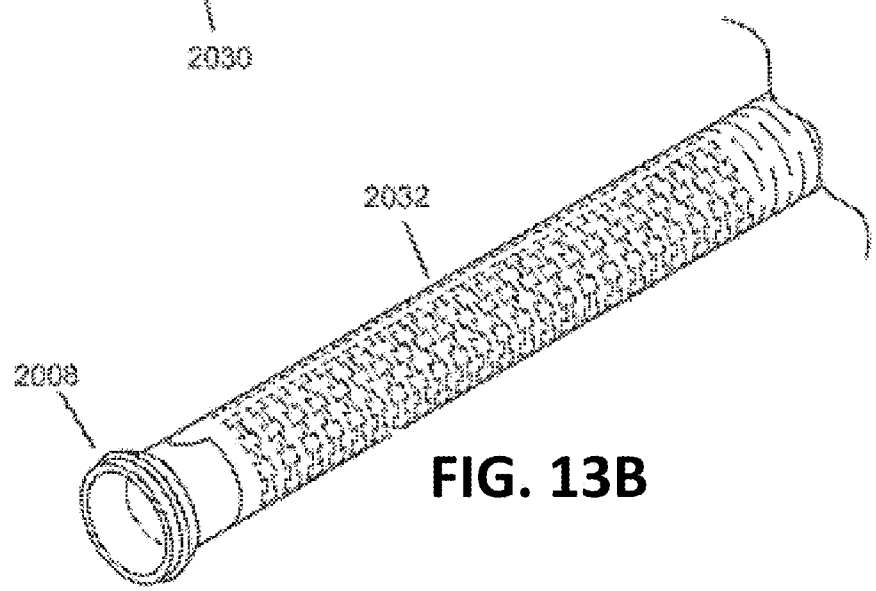
FIG. 13B depicts an assembled perspective view of the components depicted in FIG. 13A.

The inner sweep tube is inserted into the outer sweep tube, and the inner (2052) and outer alignment tabs (2042) may be brought into registration (see FIGS. 13A and 13B). The rotationally aligned inner (2052) and outer (2042) tabs may be fitted into an alignment key (2054) on the ferrule (2008) (as shown in FIG. 13B). This fitting may ensure that the inner and outer sweep tubes may be properly aligned, and may also act to prevent relative rotation between the inner and outer sweep tubes. In some variations, and the inner and outer sweep tubes may be fixed to the proximal end of the ferrule (e.g., by welding). As mentioned above (and as shown in FIG. 13A), when the inner (2052) and outer (2042) tabs are rotationally aligned, the spine of the outer sweep tube (2042) may axially aligned with the open cuts (2048) of the inner sweep tube (2030) (i.e., the spine (2050) of the inner sweep tube (2030) may rotationally spaced 180° from the spine (2040) of the outer sweep tube (2032)).

As FIG. 13A also shows, the proximal end of the inner sweep tube (2030) may include includes an open boot region (2054) facing at an angle (e.g., about 90°) from the pattern of open dovetail cuts. The open boot region (2054) may be sized and configured to receive the distal end of the inner catheter shaft. It is the inner catheter shaft that may apply a bending force to the deflecting assemblage, as will be described in greater detail later.

(iii) The Inner Catheter Shaft

The inner catheter shaft (2028) of the atherectomy apparatus (2000) shown in FIGS. 12A and 12B may be sized and configured and fabricated in generally the same manner as any of the catheter bodies previously described (e.g., such as the catheter bodies described above). For example, the inner catheter shaft (2028) may be formed from a metal tube (e.g., a 304 stainless steel tube), and may have dimensions suitable to allow the inner catheter shaft (2028) to fit within the outer catheter shaft and to accommodate passage of the torque shaft and conveyor element therein. Representative embodiments will be described.

The tube of this material and configuration will provide a baseline column stiffness, tensile stiffness, torsional stiffness, and bending stiffness. In some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability.

In some instances, there may be a gap between the inner and outer catheter such shafts, such that flushing fluid that may be conveyed down to the cutter assembly, for mixing with occlusive material within the cutter assembly. Mixing the fluid with the occlusive materials may form a slurry, which may reduce the viscosity of the materials cut, captured, and conveyed from the vessel by the atherectomy apparatus to reduce the load imposed on the cutter assembly and facilitate the transfer of materials into the waste receptacle, as has been previously described. An increased gap may provide a greater volume of fluid to the cutter assembly, which may in turn improve the mechanical conveyance of occlusive materials away from the long total occlusion, thereby reducing the chance of cutter overload and stalling.

(iv) The Mechanism of Deflection and Sweep

The distal end of the inner catheter shaft may be coupled to the inner sweep tube, and may control deflection of the catheter assembly. For example, in the variation of atherectomy apparatus (2000) described above with respect to FIGS. 12A, 12B, 13A and 13B, the inner coupler (2038) may connect the inner catheter shaft (2028) to the inner sweep tube (2030) via the boot region (2054). Generally, the inner coupler (2038) may join the inner catheter shaft (2028) to the boot region (2054) in a manner that may transmit axial compression or tensile forces to the inner sweep tube (2030), but accommodates relative rotation between the inner catheter shaft (2028) and the inner sweep tube (2028) (i.e., the inner catheter shaft does not rotate when the outer catheter shaft is rotated to rotate the inner and outer sweep tubes).

In the situation where the diameter of the inner catheter shaft is reduced to increase the gap dimension between the inner catheter shaft and the outer catheter shaft (as previously described, to accommodate a greater fluid volume), the coupling sleeve may be sized to locally step-up the distal diameter of the reduced diameter inner catheter shaft where it is coupled to the open boot of the inner sweep sleeve (i.e., the inner sweep tube need not be downsized when the inner catheter shaft is downsized), but it should be appreciated that in some instances the diameters of these components may be the same.

The proximal end of the inner catheter shaft may be coupled to a control knob (2056) on the handle (2002). The control knob (2056) may be advanced axially (distally) to advance the inner catheter shaft (2028) against the inner sweep tube (2030), to thereby apply a compressive force (as illustrated by arrow (2058) in FIG. 13D) along the inner catheter shaft (2028) to the inner sweep tube (2030). Being constrained from axial advancement by the ferrule (2008), the inner sweep tube may preferentially deflect in response to the applied compressive force in the direction of the open cut regions (as illustrated by arrow (2060) in FIG. 13D). Likewise, the control knob may be retracted axially (proximally) to relieve the compression force and apply a tensile force to the inner sweep tube, to straighten the delectable assembly, as shown in FIG. 13C.

Figure 13C:
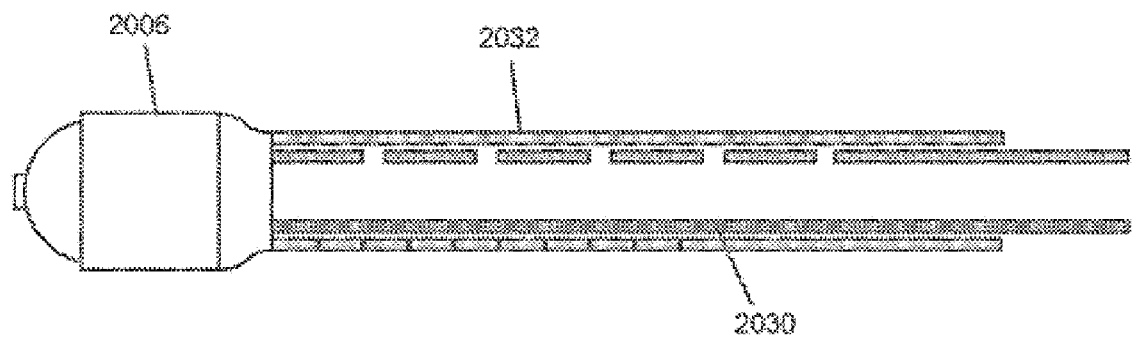
FIGS. 13C and 13D depict a manner in which the atherectomy system shown in FIGS. 12A and 12B may be manipulated.
Figure 13D:
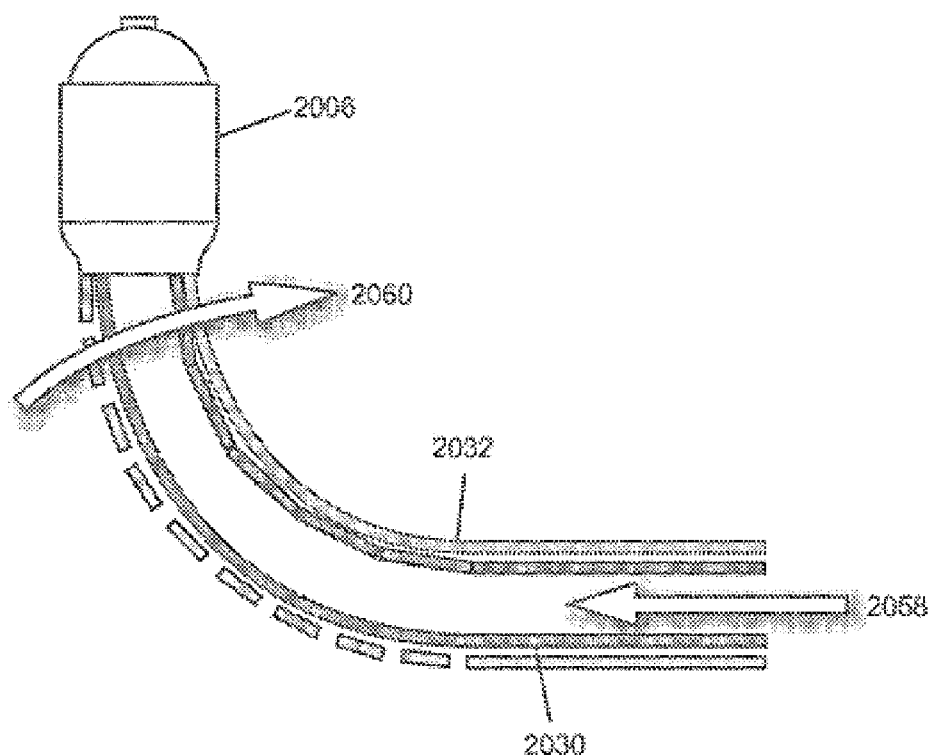

As shown in FIGS. 13C and 13D, with the spine of the inner sweep tube aligned opposite the spine of the outer sweep tube, the preferential bending property of the inner sweep tube (in the direction of the open cuts) may be unified with the preferential bending property of the concentric outer sweep tube (in the direction of the spine, away from the close cuts). The inner sweep tube may progressively bend in response to the bending force imparted by axial advancement of the inner catheter shaft, which may cause the open cuts of the inner sweep tube close and interfere first at the distal end, followed in succession by closing and interference of the proximal cuts down the length of the inner sweep tube. This may form a progressive distal-to-proximal stacking pattern as the inner sweep tube progressively bends until all cuts on the inner sweep tube close and interfere to define the full bend radius (which in some variations may be about 1°). The outer sweep tube may bend in concert with the inner sweep tube, which may open the closed cuts in a distal-to-proximal stacking pattern. The inner and outer sweep tubes may channel the applied bending force in the direction of preferential bending, and may require less bending force for a given angular unit of deflection. Further, the successive distal-to-proximal stacking of the inner sweep tube cuts and opening of the outer sweep tube cuts may result in a uniform column stiffness applied to the cutter assembly regardless of the degree of deflection.

When deflected, the catheter assembly may apply an apposition force upon the cutter assembly, which may be created by opposing contact of the outer catheter assembly against an opposite vessel wall when the cutter assembly (deflected at the end of the catheter) contacts the occlusive materials at a desirable attack angle (as shown FIGS. 19B and 19C). The unified cooperation of the inner and outer sweep tubes during preferential bending may increase the magnitude of the apposition force, and may improve trackability and avoid trauma during advancement over the guide wire.

In some variations, the outer catheter shaft may be coupled to a post on the handle that may be sized and configured to rotate in response to rotation of the control knob (2056). While axial advancement of the control knob (2056) applies compressive force to the inner catheter shaft to deflect the cutter assembly (as described in more detail above), rotation of the control knob (2056) may apply a torque to the outer catheter shaft to rotate the cutter assembly. The cutter assembly may sweep in an arc within the vessel, to clear a diameter of occlusive materials that is greater than the outer diameter of the cutter assembly. It may also be possible to apply torque to the outer catheter shaft by rotating the handle itself. Selective rotation of the cutter assembly can thus be finely controlled by a combination of control knob manipulation and handle twisting.

An indexing mechanism may be provided to provide stepwise control of deflection and/or sweeping, with tactile and/or audible feedback, so that a user may maintain knowledge of the rotation.

(v) Passive and Active Steering

The enhanced, preferential bending properties of the trackable, deflectable catheter assembly may provide the capability to both actively and passively steer the atherectomy apparatus through tortuous intravascular anatomy. FIGS. 14A-14F(5) depict a manner by which the atherectomy apparatus (2000) described above in relation to FIGS. 12A and 12B may be actively and passively steered within a vessel.

Figure 14A:
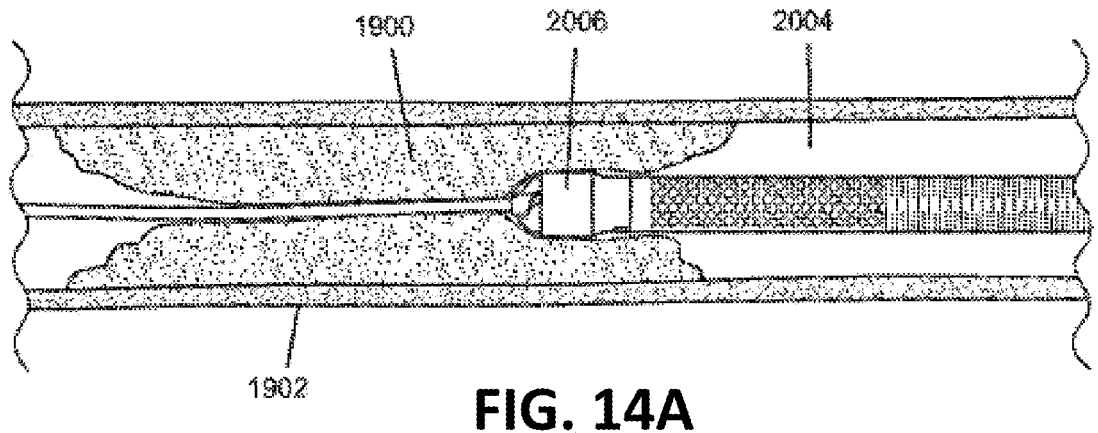
Figure 14B:
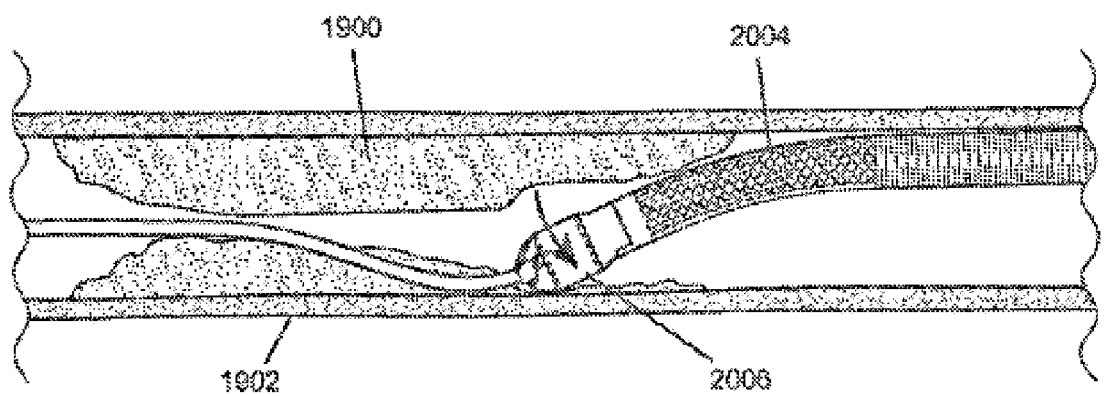
Figure 14C:
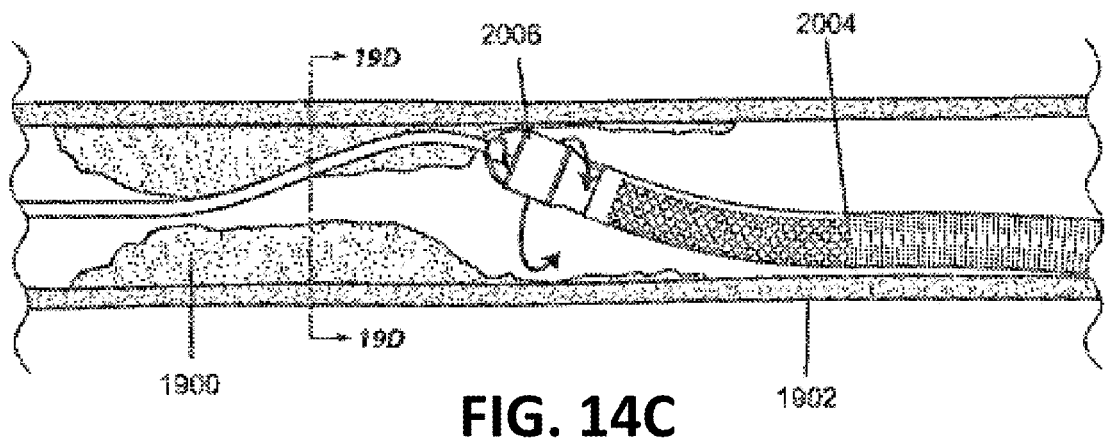
Figure 14D:
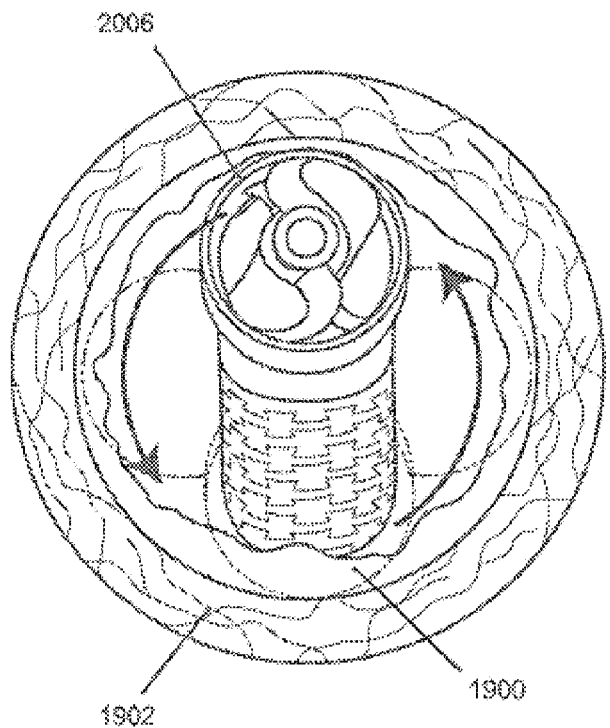
Figure 14E:
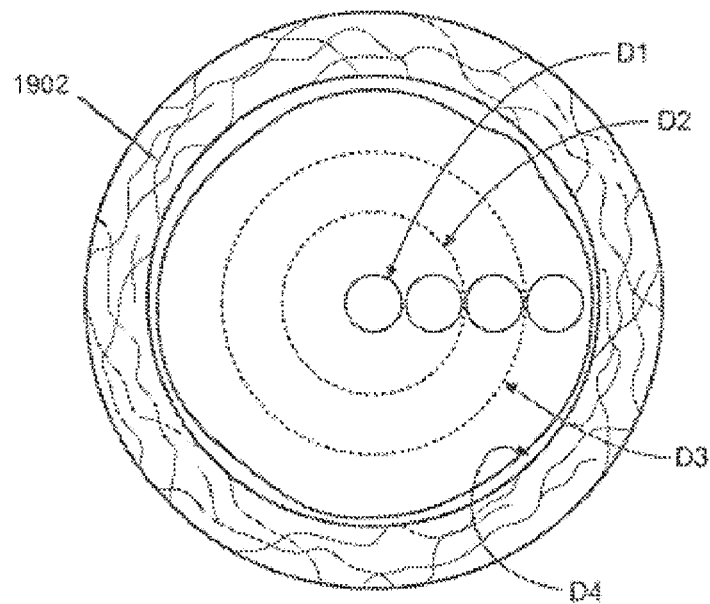

Active steering may be accomplished by advancement of the inner catheter shaft to bend the distal catheter assembly, accompanied by rotation of the catheter assembly, to point the cutter assembly in a preferred direction through an intravascular path, with or without a guide wire, and/or to point the cutter assembly toward a side wall of a vessel, with apposition, to cut and capture occlusive materials. For example, the cutter assembly (2006) of atherectomy apparatus (2000) may be advanced into occlusive material (1900) in a vessel (1902), as shown in FIG. 14A. When in place in the vessel, the catheter assembly (2004) may be deflected as shown in FIG. 14B. The deflected catheter assembly (2004) may be rotated to sweep the cutter assembly (2006), as shown in FIGS. 14C and 14D. This sweep may cause the cutter assembly to move in an arc that is greater than the outer diameter of the cutter assembly. In some variations, the cutter assembly (2006) may cut in a diameter (D2 as shown in FIG. 14E) at least two times the diameter of the cutter assembly (D1 as shown in FIG. 14E). In other variations, the cutter assembly (2006) may cut in a diameter (D3 as shown in FIG. 14E) at least three times the diameter of the cutter assembly. In still other variations, the cutter assembly (2006) may cut in a diameter (D4 as shown in FIG. 14E) at least four times the diameter of the cutter assembly.

Passive steering may be accomplished without advancement of the inner catheter shaft, when the cutter assembly (2006) encounters a bend in the intravascular path (see FIG. 14F-1). Once the cutter assembly approaches or contacts the bend, the caregiver may rotate the outer catheter body (and thus the deflected catheter assembly) into an orientation in which the preferential deflection direction faces away from the inside radius of the bend (see FIGS. 14F-2 and 14F-3). In the representative embodiment, this orientation may face the alignment key (2054) on the ferrule away from the inner radius of the bend (as can be seen in FIG. 14F-3). Due to the preferential bending properties of the catheter assembly when in this orientation, subsequent advancement of the outer catheter shaft, without concurrent advancement of the inner catheter shaft, may apply enough compression force to cause deflection of the catheter assembly in the preferential direction (i.e., away from the inside radius of the bend). Continuance of the compression force upon the catheter body may cause the catheter body to follow the passively deflected catheter assembly away from inside radius of the bend and into the bend itself (see FIGS. 14F-3 and 14F-4).

Successive bends in a tortuous path may be navigated in the same passive manner, by rotating the catheter body at each successive bend (e.g., by rotating the control knob or by rotation of the handle itself) to orient the preferential deflection of the catheter assembly away from the respective inner bend radius, and without the need to actively steer by manipulation of the inner catheter shaft.

In some variations, the catheter assembly (2004) may include one or more radiographic markings to indicate during radiographic guidance the orientation of the preferential bend direction of the catheter assembly, whether left, or right, or toward the viewer, or away from the viewer. al position of the cutter assembly without taking their eye off the radiographic image.

FIGS. 15A and 15B depict another variation of an atherectomy apparatus (1600) described here. As shown there, atherectomy apparatus (1600) may comprise a first catheter (1602), a second catheter (1604), and a cutter assembly (1605) attached to the first catheter (1602). The first catheter (1602) may be moveable relative to the second catheter (1604) to move a distal portion of the atherectomy apparatus (1600) between an undeflected configuration (as shown in FIG. 15A) and a deflected configuration (as shown in FIG. 15B). In the variation of atherectomy apparatus (1600) shown in FIGS. 15A and 15B, the first catheter (1602) may be moveable within the second catheter (1604), although it should be appreciated that in other variations the second catheter (1604) may be slidable within the first catheter (1602).

Generally, a distal portion (1606) of the second catheter (1604) may be shaped to take on a deflected position as shown in FIG. 15B. Specifically, the deflected distal portion (1606) may comprise a double curve having a first proximal curve (1608) and a second distal curve (1610). As shown there, the first curve (1608) may bend the distal portion (1606) away from the longitudinal axis (1612) of a proximal portion of the second catheter (1604), while the second curve (1610) may bend the distal portion (1606) in a direction toward the longitudinal axis (1612). The double-curve configuration of the distal portion (1606) may allow the second curve (1610) to contact or otherwise rest against a wall (1614) of a blood vessel (1616), as shown in FIG. 15B. Additionally, this may angle the cutter assembly (1605) toward an opposite vessel wall (1618) during cutting. In instances when the atherectomy apparatus (1600) is advanced over a guide wire (1620) as shown in FIG. 15B, the guide wire (1620) may contact the opposite vessel wall (1618) and may help to prevent the cutter assembly (1605) from directly contacting and/or damaging the vessel wall (1618). In some instances, the double-curve configuration of the distal portion (1606) may allow for advancement of the distal portion (1606) while deflected while minimizing the risk that the cutter assembly (1605) may catch on tissue and retroflex.

As mentioned above, the first catheter (1602) may be moved relative to the second catheter (1604) to move the atherectomy apparatus between deflected and undeflected configurations. Specifically, the first catheter (1602) may comprise a distal portion (1622) and a proximal portion (not shown), where the distal portion (1622) is more flexible than the proximal portion. Additionally, the distal portion (1622) of the first catheter (1602) may be more flexible than the distal portion (1606) of the second catheter (1604), while the proximal portion of the first catheter (1602) may be stiffer than the distal portion (1606) of the second catheter (1604). Accordingly, the first catheter (1602) may be advanced such that the flexible distal portion (1622) of the first catheter (1602) extends beyond the distal end of the second catheter (1604), which may the proximal portion of the first catheter (1602) within the distal portion (1606) of the second catheter (1604) (or around the distal portion (1606) of the second catheter (1604) in variations where the second catheter (1604) is positioned inside the first catheter (1602). Because the proximal portion of the first catheter (1602) is stiffer than the distal portion of the second catheter (1604), axial alignment of these catheter segments may cause the proximal portion of the first catheter (1602) to straighten out the curves of the distal portion of the second catheter (1604), thereby placing the atherectomy apparatus (1600) in an undeflected configuration, as shown in FIG. 15A. Because the flexible distal portion of the first catheter (1602) extends beyond the distal portion of the second catheter (1604) when in an undeflected configuration, it may be used to track the cutter assembly (1605) along a guide wire during navigation of the atherectomy apparatus (1600) through the vasculature. Additionally, the atherectomy apparatus (1600) may be advanced while cutting to cut along the path of the guide wire (which may be a straight path in some instances), as described in more detail below. The atherectomy apparatus (1600) may then be withdrawn and deflected to cut a larger path through occlusive material (not shown), such as described below.

To move the atherectomy apparatus to a deflected configuration, the first catheter (1602) may be withdrawn to place the flexible distal portion (1622) of the first catheter (1602) in axial alignment with the distal portion (1606) of the second catheter (1604). Because the distal portion (1606) of the second catheter (1604) is stiffer than the distal portion (1622) of the first catheter (1602), the second catheter (1604) may cause the flexible distal portion (1622) of the first catheter (1602) to take on the dual-curve configuration described above with respect to FIG. 15B.

III. Imaging Assemblies for Use with Atherectomy Devices

Atherectomy systems of the invention include an imaging assembly (e.g., 311, 511, 2011) that provides for guided cutting and removal of occlusions. The imaging assembly may be and ultrasound imaging assembly, photoacoustic imaging assembly, optical coherence tomography imaging assembly, or combination thereof. In advanced embodiments, the systems of the invention incorporate focused acoustic computed tomography (FACT), which is described in WO2014/109879.

The imaging assembly may be an intravascular ultrasound (IVUS) imaging assembly. The ultrasound probe can either be either a rotating transducer or an array of circumferentially positioned transducers. The proximal end of the catheter is attached to computerized imaging console. The IVUS imaging element (i.e. ultrasound probe) includes transducers that image the tissue with ultrasound energy (e.g., 20-50 MHz range) and image collectors that collect the returned energy (echo) to create an intravascular image. The imaging transducers and imaging collectors are coupled to signal lines that run through the length of the catheter and couple to the computerized ultrasound equipment.

IVUS imaging assemblies produce ultrasound energy and receive echoes from which real time ultrasound images of a thin section of the blood vessel are produced. The imaging transducers of the imaging element are constructed from piezoelectric components that produce sound energy at 20-50 MHz. The image collectors of the imaging element comprise separate piezoelectric elements that receive the ultrasound energy that is reflected from the vasculature. Alternative embodiments of imaging assembly may use the same piezoelectric components to produce and receive the ultrasonic energy, for example, by using pulsed ultrasound. That is, the imaging transducer and the imaging collectors are the same. Another alternative embodiment may incorporate ultrasound absorbing materials and ultrasound lenses to increase signal to noise.

IVUS data is typically gathered in segments where each segment represents an angular portion of an IVUS image. Thus, it takes a plurality of segments (or a set of IVUS data) to image an entire cross-section of a vascular object. Furthermore, multiple sets of IVUS data are typically gathered from multiple locations within a vascular object (e.g., by moving the transducer linearly through the vessel). These multiple sets of data can then be used to create a plurality of two-dimensional (2D) images or one three-dimensional (3D) image.

IVUS imaging assemblies and processing of IVUS data are described in further detail in, for example, Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et at., U.S. Pat. No. 5,373, 845, Seward et al., Mayo Clinic Proceedings 71(7):629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et at., U.S. Pat. No. 5,183, 048, Eberle et al., U.S. Pat. No. 5,167,233, Eberle et at., U.S. Pat. No. 4,917,097, Eberle et at., U.S. Pat. No. 5,135,486, U.S. Pub. 2009/0284332; U.S. Pub. 2009/0195514 A1; U.S. Pub. 2007/0232933; and U.S. Pub. 2005/0249391 and other references well known in the art relating to intraluminal ultrasound devices and modalities.

OCT is a medical imaging methodology using a miniaturized near infrared light-emitting probe. As an optical signal acquisition and processing method, it captures micrometer-resolution, three-dimensional images from within optical scattering media (e.g., biological tissue). Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety.

In OCT, a light source delivers a beam of light to an imaging device to image tar tissue. Light sources can include pulsating light sources or lasers, continuous wave light sources or lasers, tunable lasers, broadband light source, or multiple tunable laser. Within the light source is an optical amplifier and a tunable filter that allows a user to select a wavelength of light to be amplified. Wavelengths commonly used in medical applications include near-infrared light, for example between about 800 nm and about 1700 nm.

Aspects of the invention may obtain imaging data from an OCT system, including OCT systems that operate in either the time domain or frequency (high definition) domain. Basic differences between time-domain OCT and frequency-domain OCT is that in time-domain OCT, the scanning mechanism is a movable mirror, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference mirror, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images. In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously.

Alternatively, in swept-source OCT, the interference spectrum is recorded by using a source with adjustable optical frequency, with the optical frequency of the source swept through a rang of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in its entirety.

According to certain aspects of the invention, the obtained image data from the imaging assembly of the atherectomy systems described herein is processed to characterize biological material and/or foreign material (i.e. the occlusion) within the vessels. The characterization allows one to determine with specificity the type of occlusion within the vessel (e.g. plaque or clot) and the severity of the occlusion, e.g., whether the occlusion is calcified, fibrous, or soft. The processing step may be performed by an image processing computer operably connected to the imaging assembly via signal wires.

Figure 16:
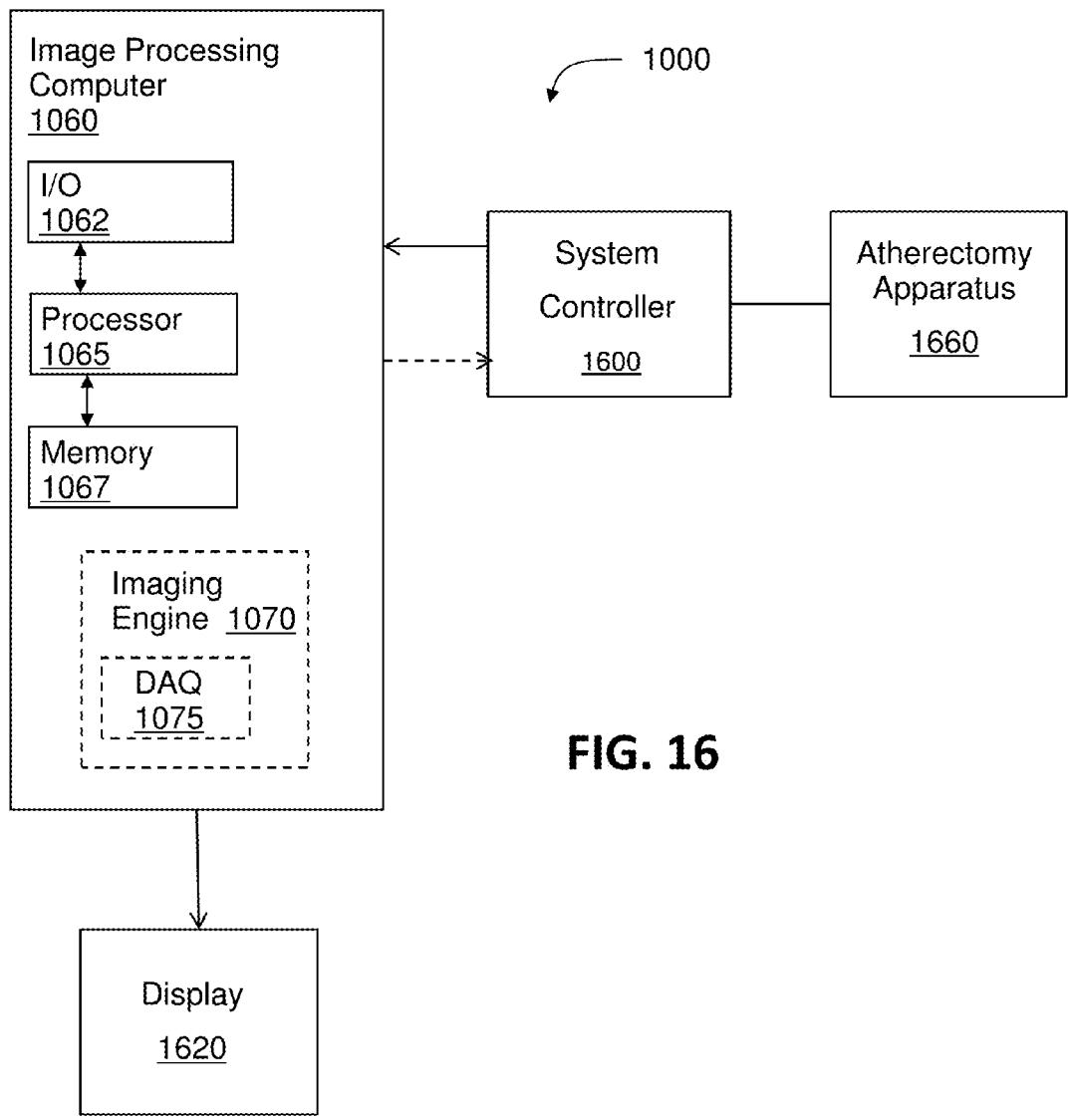
FIG. 16 illustrates a system for uses with atherectomy apparatuses described herein.

Referring now to FIG. 16, the atherectomy system 10 may be coupled to and coordinated by a system controller 600. The system controller 1600 may control the timing, duration, and amount of imaging. Accordingly to certain embodiments, the system controller 1600 may also control the rotation of the torque shaft (and cutting elements coupled thereto) and may also rotation of the catheter body (and imaging assemblies and housing coupled thereto). As shown in FIG. 17, the system controller 1600 is additionally interfaced with image processing computer 1060. According to certain embodiments, the processor 1065 of the image processing computer 1060 performs tissue/blood characterization, thereby allowing the viewed and assessed images to be the basis for defining parameters for complete treatment and dissolution of the blockage. The system 1000 also includes a display 1620 and a user interface that allow a user, e.g. a surgeon, to interact with the images (including tissue characterization) and to control the parameters of the treatment.

As shown in FIG. 16, a system controller 1600 is interfaced to an image processing computer 1060 that is capable of synthesizing the images into easy-to-understand images. The image processing computer 1060 is also configured to analyze the spectrum of the collected data to determine tissue characteristics, a.k.a. virtual histology. As discussed in greater detail below, the image processing will deconvolve the reflected acoustic waves or interfered infrared waves to produce distance and/or tissue measurements, and those distance and tissue measurements can be used to produce an image, for example an IVUS image or an OCT image. Flow detection and tissue characterization algorithms, including motion-detection algorithms (such as CHROMAFLO (IVUS fluid flow display software; Volcano Corporation), Q-Flow, B-Flow, Delta-Phase, Doppler, Power Doppler, etc.), temporal algorithms, harmonic signal processing, can be used to differentiate blood speckle from other structural tissue, and therefore enhance images where ultrasound energy back scattered from blood causes image artifacts.

In certain embodiments, the image processing may additionally include spectral analysis, i.e., examining the energy of the returned acoustic signal at various frequencies. Spectral analysis is useful for determining the nature of the tissue and the presence of foreign objects. A plaque deposit or neointimal hyperplasia, for example, will typically have different spectral signatures than nearby vascular tissue without such plaque or neointimal hyperplasia, allowing discrimination between healthy and diseased tissue. Also a metal surface, such as a AV graft, will have a different spectral signal. Such signal processing may additionally include statistical processing e.g., averaging, filtering, or the like) of the returned ultrasound signal in the time domain. The spectral analysis can also be used to determine the tissue lumen/blood border. Other signal processing techniques known in the art of tissue characterization may also be applied. By distinguishing the between the above referenced features within the vessel, one is able to carefully dissolve the blockage without disrupting the surrounding vessel tissue.

Other image processing may facilitate use of the images or identification of features of interest. For example, the border of a lumen may be highlighted or thrombus or plaque deposits may be displayed in a visually different manner by assigning thrombus a discernible color) than other portions of the image. Other image enhancement techniques known in the art of imaging may also be applied. In a further example, similar techniques can be used to discriminate between vulnerable plaque and other plaque, or to enhance the displayed image by providing visual indicators to assist the user in discriminating between vulnerable and other plaque. Other measurements, such as flow rates or pressure may be displayed using color mapping or by displaying numerical values. In some embodiments, the open cross-sectional area of the lumen is colorized with red to represent the blood flux. Thus, by using virtual histology (spectral analysis), methods of the invention allow one to assess the blockage before, during, and after treatment.

In addition to the above disclosed systems, the following systems for detecting and characterizing plaque and biological tissue using virtual histology are disclosed in U.S. Pat. No. 6,200,268 entitled "VASCULAR PLAQUE CHARACTERIZATION" issued Mar. 13, 2001, U.S. Pat. No. 6,381,350 entitled "INTRAVASCULAR ULTRASONIC ANALYSIS USING ACTIVE CONTOUR METHOD AND SYSTEM" issued Apr. 30, 2002, U.S. Pat. No. 7,074,188 entitled "SYSTEM AND METHOD OF CHARACTERIZING VASCULAR TISSUE" issued Jul. 11, 2006, U.S. Pat. No. 7,175,597 entitled "NON-INVASIVE TISSUE CHARACTERIZATION SYSTEM AND METHOD" issued Feb. 13, 2007, U.S. Pat. No. 7,215,802 entitled "SYSTEM AND METHOD FOR VASCULAR BORDER DETECTION" issued May 8, 2007, U.S. Pat. No. 7,359,554 entitled "SYSTEM AND METHOD FOR IDENTIFYING A VASCULAR BORDER" issued Apr. 15, 2008, and U.S. Pat. No. 7,463,759 entitled "SYSTEM AND METHOD FOR VASCULAR BORDER DETECTION" issued Dec. 9, 2008.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A catheter device comprising:
a catheter body having first and second internal lumens, wherein the first internal lumen extends from a proximal end of the catheter body to an opening in a proximal end of a housing fixed to a distal end of the catheter body, wherein a diameter of the housing is greater than a diameter of the catheter body;
a torque shaft disposed within the first lumen of the catheter body and defining the second lumen therein;
first and second cutting elements each having cutting edges, the first cutting element extending through an opening in a distal end of the housing from a distal end of the second cutting element, the second cutting element having a proximal end fixed to the distal end of the torque shaft and a distal end fixed to a proximal end of the first cutting element, the housing surrounding the distal end of the torque shaft and the second cutting element, wherein a diameter of the first and second cutting elements is greater than the diameter of the catheter body;
an imaging element circumferentially surrounding and fixed to the housing, wherein the imaging element is configured to communicate with a signal processor via one or more signal wires extending from the imaging element through the second internal lumen to the proximal end of the catheter body, wherein the one or more signal wires are configured for transmitting signals from the signal processor to the imaging element and for transmitting signals back from the imaging element to the signal processor;

a discharge element operably associated with the catheter body, the discharge element configured to receive occlusive material morcellated by the first and second cutting elements;

wherein the catheter body, the housing at the distal end of the catheter body and the imaging element are configured to rotate in an opposite direction of the torque shaft, wherein the cutting edges of the first cutting element include cutting blades, and the first cutting element further includes blunt crushing elements interposed between the cutting blades, wherein a distal surface of each of the blunt crushing elements is flat, and edges of the blunt crushing elements leading to the distal surface are sharp, and wherein a height of a distal end of each cutting blade is greater than a height of the distal surface of each blunt crushing element in a longitudinal direction from a proximal base of the first cutting element.

2. The catheter device of claim 1, wherein the one or more signal wires comprises an optical fiber, and wherein at least some of the imaging signals are optical signals transmitted on the optical fiber.

3. The catheter device of claim 1, wherein the imaging element comprises an ultrasound transducer.

4. The catheter device of claim 3, wherein the ultrasound transducer is a phased-array transducer.

5. The catheter device of claim 4, wherein the ultrasound transducer is configured to image in a plane distal to the ultrasound transducer.

6. The catheter device of claim 1, wherein each of the cutting elements comprises at least two helical flutes.

7. The catheter device of claim 1 further comprising a conveying element proximal to the second cutting element.

8. The catheter device of claim 7, wherein the conveying component comprises a helical wire wound about the torque shaft.

9. The catheter device of claim 8, wherein the helical wire has a substantially rectangular cross-section.

10. A system comprising:
a signal processor; and
a catheter device comprising:
  a catheter body configured for insertion into an associated blood vessel, the catheter body having first and second internal lumens, wherein the first internal lumen extends from a proximal end of the catheter body to an opening in a proximal end of a housing fixed to a distal end of the catheter body, wherein a diameter of the housing is greater than a diameter of the catheter body;
  torque shaft disposed within the first lumen of the catheter body and defining the second lumen therein;
  first and second cutting elements each having cutting edges, the first cutting element extending through an opening in a distal end of the housing from a distal end of the second cutting element, the second cutting element having a proximal end fixed to the distal end of the torque shaft and a distal end fixed to a proximal end of the first cutting element, the housing surrounding the distal end of the torque shaft and the second cutting element, wherein a diameter of the first and second cutting elements is greater than the diameter of the catheter body;
  an imaging element circumferentially surrounding and fixed to the housing, wherein the imaging element is connected to communicate with the signal processor via one or more signal wires extending from the imaging element through the second internal lumen to the proximal end of the catheter body, wherein the one or more signal wires are connected to transmit signals from the signal processor to the imaging element and to transmit imaging signals back from the imaging element to the signal processor; and
  a discharge element operably associated with the catheter body, the discharge element configured to receive occlusive material morcellated by the cutting element;
wherein the imaging element comprises an ultrasound imaging element or an optical coherence tomography (OCT) imaging element,
wherein the signal processor is configured to perform spectral analysis of the imaging signals to determine tissue characteristics of an occlusion and/or tissue of the associated blood vessel,
wherein the cutting edges of the first cutting element include cutting blades, and
the first cutting element further includes blunt crushing elements interposed between the cutting blades, wherein a distal surface of each of the blunt crushing elements is flat, and edges of the blunt crushing elements leading to the distal surface are sharp, and
wherein a height of a distal end of each cutting blade is greater than a height of the distal surface of each blunt crushing element in a longitudinal direction from a proximal base of the first cutting element.

11. The system of claim 10, wherein the signal processor is configured to determine a density of the occlusion.

12. The system of claim 10, wherein the signal processor is configured to determine a composition of the occlusion.

13. The system of claim 10, wherein the signal processor is configured to determine a blood-tissue border of a lumen of the associated blood vessel by the spectral analysis.

14. The system of claim 10, wherein the signal processor is configured to differentiate blood flow through the associated blood vessel by flow detection, motion detection, or blood speckle detection.

15. The system of claim 10, further comprising:
a display configured to display images generated from the imaging signals by the signal processor including a graphical representation of the determined tissue characteristics of the occlusion and/or tissue of the associated blood vessel.

16. A system comprising:
a signal processor; and
a catheter device comprising:
  a catheter body configured for insertion into an associated blood vessel, the catheter body having first and second internal lumens, wherein the first internal lumen extends from a proximal end of the catheter body to an opening in a proximal end of a housing fixed to a distal end of the catheter body, wherein a diameter of the housing is greater than a diameter of the catheter body;
  a torque shaft disposed within the first lumen of the catheter body and defining the second lumen therein;
  first and second cutting elements each having cutting edges, the first cutting element extending through an opening in a distal end of the housing from a distal end of the second cutting element, the second cutting element having a proximal end fixed to the distal end of the torque shaft and a distal end fixed to a proximal end of the first cutting element, the housing surrounding the distal end of the torque shaft and the second cutting element, wherein a diameter of the first and second cutting elements is greater than the diameter of the catheter body;

and an imaging element circumferentially surrounding and fixed to the housing, wherein the imaging element is connected to communicate with the signal processor via one or more signal wires extending from the imaging element through the second internal lumen to the proximal end of the catheter body, wherein the one or more signal wires are connected to transmit signals from the signal processor to the imaging element and to transmit imaging signals back from the imaging element to the signal processor;

wherein the imaging element comprises an ultrasound imaging element or an optical coherence tomography (OCT) imaging element, wherein the signal processor is configured to perform spectral analysis of the imaging signals by examining the energy of the returned acoustic signal at various frequencies to determine tissue characteristics of an occlusion and/or tissue of the associated blood vessel, wherein the cutting edges of the first cutting element include cutting blades, and the first cutting element further includes blunt crushing elements interposed between the cutting blades, wherein a distal surface of each of the blunt crushing elements is flat, and edges of the blunt crushing elements leading to the distal surface are sharp, and wherein a height of a distal end of each cutting blade is greater than a height of the distal surface of each blunt crushing element in a longitudinal direction from a proximal base of the first cutting element.

17. The system of claim 16, wherein the signal processor is configured to determine a density and/or composition of the occlusion.

18. The system of claim 16, wherein the signal processor is configured to differentiate blood flow through the associated blood vessel by flow detection, motion detection, or blood speckle detection.

* * * * *